US008349816B2

(12) United States Patent
El-Gewely

(10) Patent No.: US 8,349,816 B2
(45) Date of Patent: *Jan. 8, 2013

(54) ANTIBACTERIAL TREATMENT OF OSTEOARTHRITIS

(75) Inventor: Mohamed Raafat El-Gewely, Tomasjord (NO)

(73) Assignee: Orthogenics AS, Tromso (NO)

( * ) Notice: Subject to any disclaimer, the term of this patent is extended or adjusted under 35 U.S.C. 154(b) by 546 days.

This patent is subject to a terminal disclaimer.

(21) Appl. No.: 11/703,887

(22) Filed: Feb. 7, 2007

(65) Prior Publication Data

US 2008/0027013 A1 Jan. 31, 2008

Related U.S. Application Data

(62) Division of application No. 10/480,775, filed as application No. PCT/GB02/02771 on Dec. 15, 2003.

(51) Int. Cl.
*A61K 31/65* (2006.01)
*A61K 31/70* (2006.01)
(52) U.S. Cl. ............... 514/152; 514/29; 514/38; 514/39
(58) Field of Classification Search .................... 514/152
See application file for complete search history.

(56) References Cited

U.S. PATENT DOCUMENTS

| 5,874,592 | A | * | 2/1999 | Tanaka et al. .................. 549/331 |
| 6,165,999 | A | * | 12/2000 | Vu ................................. 514/152 |
| 6,475,992 | B2 | * | 11/2002 | McLean .......................... 514/37 |

FOREIGN PATENT DOCUMENTS

| EP | 0659763 | 6/1995 |
| WO | WO 98/08480 | 3/1998 |

OTHER PUBLICATIONS

Amin et al., "A novel mechanism of action of tetracyclines: effects on nitric oxide synthases," (1996) Proc. Natl. Acad. Sci. UDS 93:14014-14019.
Brandt, K.D.,"Modification by Oral Doxycycline Administration of Articular Cartilage Breakdown in Osteoarthritis," The Journal of Rheumatology (1995)21:supp43:149-51.
Brittberg et al, "Treatment of Deep cartilage defects in the knee with autologous chondrocyte transplantation," N. Engl. J. Med. 1994 Oct. 6, 331(14)889-95.
Chicurel, "Slimebusters,"Nature (2000) 408:284-286.
Cole et al., "Doxycycline disrupts chondrocyte differentiation and inhibits cartilage matrix degradation," Arthritis and Rheumatism, (1994)37:1727-1734.
De Bastiani et al., "Use of ceftazidime in the treatment of osteomyelitis and osteoarthritis." International Journal of Clinical Pharmacology, Therapy, and Toxicology. 24(12):677-679 Dec. 1986.
Espehaug et al., "Antibiotic Phophylaxis in total hip arthroplasty," (1997) J. Bone Joint Surg. Br. Jul. 70(4) 590-595.
Fisher et al., "Development and evaluation of a broad-range of PCR-ELISA assay with *Borrelia burgdorferi* and *Streptococcus pneumoniae* as model organisms for reactive arthritis and bacterial meningitis." Journal of Microbiological Methods 40(1) 79-88 Mar. 2000.
Ghani, M. and Soothill, J.S., "Ceftazidime, gentamicin, and rifampicim, in combination kill biofilms of mucoid *Pseudomonas aerations*," Canadian Journal of Microbiology (1997) 42:999-1004.
Lucino et al., Reduction of the Severity of Canine Osteoarthritis by Prophylactic Treatment with Oral Doxycycline, Arthritis and Rheumatism, 35(10):150-159 (1992).
Nordvag et al., "Direct Use of Blood in PCR," BioTechniques (1992) 12,4:490-491.
Nordvag et al., "Direct PCR of Washed Blood Cells," Methods in Neurosciences 26:15-25 (1995).
Otero et al., "Haemophilius influenzae type b osteoarthritis. A report of 7 cases and a review of the literature." Anales Espanoles De Pediatria 49(6):594-602 Dec. 1998.
Roos et al., Development of a self-administered outcome measure. Journal of Orthopaedic and SSports Physical Therapy 78(2):88-96 (1998).
Singh et al. "Quorum,-sensing signals indicate that cystic fibrosis lungs are infected with bacterial biofilms," Nature (2000) 407:762-764.
Smith et al., "Oral Administration of Doxycycline reduces Collagenase and Gelitinase activities in extracts of human osteoarthritic cartilage," The Journal of Rheumatology (1998)25:532-535.
Tegner and Lysholm: Rating systems in the Evaluation of Knee Ligament Injuries. Clinical Orthpaedics an Related Research Number 198 Sep. 1985:43-49.
Tunney et al., "Detection of prosthetic hip infection at revision arthroplasty and immunofluorescence microscopy and PCR amplification of the bacterial 16S rRNA gene." Journal of Clinical Microbiolgy 37(10):3281-3290 Oct. 1999.
Van Der Heijden et al., "Detection of myobacteria in joint samples from patients with arthritis using a genus-specific polymerase chaim reaction and sequence analysis." Rheumatology 38(6):547-553 Jun. 1999.
Various, "46th week of rheumatology at Aix-les-Bains, France Apr. 4-6, 2001." Rheumatologie 53(3):7-13,16-24,27-36.
Wilmott et al.,"Mercaptoethylguanadine inhibits the inflammatory response in a murine model of chronic infection with *Pseudmonas aeruginosa*," The Journal of Pharacology and Experimental Therapeutics (2000)2952:1:88-95.
Yanagihara et al., "Combination therapy for chronic *Pseudmonas aeruginosa* respiratory infection associated with biofilm formation," Journal of Antimicrobial Chemotherapy (2000)46:69-72.
Yu et al, "Doxycycline inhibits type XI collagenolytic Ativity if extracts from human osteoarthritic cartiage and of gelatinase," (1991) J. Rheumatol. 18:1450-1452.
Yu et al., "Reduction of the Severity of canine osteoarthritis by prophylactic treatments with oral doxycycline," Arthritis and Rheumatism (1992)35:10:1150-1159.

(Continued)

*Primary Examiner* — Elli Peselev
(74) *Attorney, Agent, or Firm* — Ballard Spahr LLP

(57) ABSTRACT

The present invention relates to use of an antibacterial agent in the manufacture of a medicament for the treatment of osteoarthritis, more particularly for the treatment of a bacterial infection which is responsible for osteoarthritis. Also described are methods for the diagnosis of osteoarthritis through the detection of certain bacteria in an affected joint of a patient with osteoarthritis.

10 Claims, 16 Drawing Sheets

OTHER PUBLICATIONS

Birchfield PC. (2001) Osteoarthritis Overview. Geriatric Nursing. 22(3): 124-131.
Brown De, Neumann Rd. (1999) Orthopedic Secrets. (2nd Edition) Hanley & Belfus: Philadelphia, pp. 1-4 (Chapter 1) and 14-18 (Chapter 5).
Chard J, Dieppe P. (2002) Update: Treatment of Osteoarthritis. Arthritis Rheum. 47(6): 686-690.
Chitnavis J, Carr A. (2002) Chapter 2.7.15—Osteoarthritis. Textbook of Orthopedics and Trauma (Bulstrode et al. (Eds.)) Oxford University Press: New York, pp. 1406-1421.
Dieppe P. (2001) From protocols to principles, from guidelines to toolboxes: aids to good management of osteoarthritis. Rheumatology (Oxford). 40(8): 841-842.
Felson DT, Lawrence RC, Dieppe PA, Hirsch R, et al. (2000) Osteoarthritis: new insights. Part 1: the disease and its risk factors. Ann Intern Med. 133(8): 635-646.
Felson DT, Lawrence RC, Hochberg MC, McAlindon T, et al. (2000) Osteoarthritis: new insights. Part 2: treatment approaches. Ann Intern Med. 133(9): 726-737.
Nade S (2002) Chapter 2.7.18—Septic Arthritis. Textbook of Orthopedics and Trauma (Bulstrode et al. (Eds.)) Oxford University Press: New York, pp. 1437-1443.
Peat G, Croft P, Hay E. (2001) Clinical assessment of the osteoarthritis patient. Best Pract Res Clin Rheumatol. 15(4): 527-544.
Pendleton A, Arden N, Dougados M, Doherty M, Bannwarth B, et al. (2000) EULAR recommendations for the management of knee osteoarthritis: report of a task force of the Standing Committee for International Clinical Studies Including Therapeutic Trials (ESCISIT). Ann Rheum Dis. 9(12): 936-944.
Rubin BR. (2001) Osteoarthritis. JAOA. 101(4): S2-S5.
Sandell LJ, Aigner T. (2001) Articular cartilage and changes in arthritis. An introduction: cell biology of osteoarthritis. Arthritis Res. 3(2): 107-113.
Sangha O. (2000) Epidemiology of rheumatic diseases. Rheumatology (Oxford). 39 Suppl 2: 3-12.
Taylor-Robinson D, Keat A. (2001) How can a causal role for small bacteria in chronic inflammatory arthritides be established or refuted? Ann Rheum Dis. 60(3): 177-184.
Walker-Bone K, Javaid K, Arden N, Cooper C. (2000) Regular review: medical management of osteoarthritis. BMJ. 321 (7266): 936-940.
Understanding Arthritis. (2004) Web page Extract, pp. 1-8, published by Zimmer, Inc. (http://www.zimmer.com).
Voluntary Amendments filed Oct. 25, 2010 for Canadian Application No. 2,456,685, which claims priority to PCT/GB2002/002771 filed on Jun. 17, 2002 (M.R. El-Gewely is inventor; Orthogenics AS is Applicant).
Request for Reinstatement of Application filed Oct. 19, 2010 for Canadian Application No. 2,456,685, which claims priority to PCT/GB2002/002771 filed on Jun. 17, 2002 (M.R. El-Gewely is inventor; Orthogenics AS is Applicant).
Examination Report issued on Apr. 20, 2009 for Canadian Application No. 2,456,685, which claims priority to PCT/GB2002/002771 filed on Jun. 17, 2002 (M.R. El-Gewely is inventor; Orthogenics AS is Applicant).
Final Office Action issued Aug. 27, 2010 for U.S. Appl. No. 10/480,775, which claims priority to PCT/GB2002/002771 filed on Jun. 17, 2002 (M.R. El-Gewely is inventor).
Response to Non-Final Office Action filed Jun. 16, 2010 for U.S. Appl. No. 10/480,775, which claims priority to PCT/GB2002/002771 filed on Jun. 17, 2002 (M.R. El-Gewely is inventor).
Interview Summary issued Mar. 9, 2010 for U.S. Appl. No. 10/480,775, which claims priority to PCT/GB2002/002771 filed on Jun. 17, 2002 (M.R. El-Gewely is inventor).
Amendment and Response to Office Action filed Sep. 14, 2009 for U.S. Appl. No. 10/480,775, which claims priority to PCT/GB2002/002771 filed on Jun. 17, 2002 (M.R. El-Gewely is inventor).
Interview Summary issued Sep. 4, 2009 for U.S. Appl. No. 10/480,775, which claims priority PCT/GB2002/002771 filed on Jun. 17, 2002 (M.R. El-Gewely is inventor).
Advisory Action issued Apr. 28, 2009 for U.S. Appl. No. 10/480,775, which claims priority to PCT/GB2002/002771 filed on Jun. 17, 2002 (M.R. El-Gewely is inventor).
Response to Final Office Action filed Apr. 13, 2009 for U.S. Appl. No. 10/480,775, which claims priority to PCT/GB2002/002771 filed on Jun. 17, 2002 (M.R. El-Gewely is inventor).
Notice of Appeal filed Feb. 12, 2009 for U.S. Appl. No. 10/480,775, which claims priority to PCT/GB2002/002771 filed on Jun. 17, 2002 (M.R. El-Gewely is inventor).
Final Office Action issued Aug. 13, 2008 for U.S. Appl. No. 10/480,775, which claims priority to PCT/GB2002/002771 filed on Jun. 17, 2002 (M.R. El-Gewely is inventor).
Communication under Rule 71(3) EPC (Examining Division intends to grant EP patent) issued Mar. 31, 2010 for European Application No. 02730515.0-2112, which claims priority to PCT/GB2002/002771 filed on Jun. 17, 2002 (M. R. El-Gewely is inventor; Orthogenics AS is Applicant).
Minutes in Accordance with Rule 12(4) EPC issued Mar. 24, 2010 for European Application No. 02730515.0-2112, which claims priority to PCT/GB2002/002771 filed on Jun. 17, 2002 (M.R. El-Gewely is inventor; Orthogenics AS is Applicant).
Brief Communication issued Mar. 2, 2010 for European Application No. 02730515.0-2112, which claims priority to PCT/GB2002/002771 filed on Jun. 17, 2002 (M.R. El-Gewely is inventor; Orthogenics AS is Applicant).
Brief Communication issued Feb. 18, 2010 for European Application No. 02730515.0-2112, which claims priority to PCT/GB2002/002771 filed on Jun. 17, 2002 (M.R. El-Gewely is inventor; Orthogenics AS is Applicant).
Queries to the Examiner filed Feb. 17, 2010 for European Application No. 02730515.0-2112, which claims priority to PCT/GB2002/002771 filed on Jun. 17, 2002 (M.R. El-Gewely is inventor; Orthogenics AS is Applicant).
Response to Summons filed Feb. 3, 2010 for European Application No. 02730515.0-2112, which claims priority to PCT/GB2002/002771 filed on Jun. 17, 2002 (M.R. El-Gewely is inventor; Orthogenics AS is Applicant).
Summons to Attend Oral Proceedings issued Sep. 25, 2009 for European Application No. 02730515.0-2112, which claims priority to PCT/GB2002/002771 filed on Jun. 17, 2002 (M.R. El-Gewely is inventor; Orthogenics AS is Applicant).
Response to Communication pursuant to 94(3) EPC filed Jun. 26, 2008 for European Application No. 02730515.0-2112, which claims priority to PCT/GB2002/002771 filed on Jun. 17, 2002 (M.R. El-Gewely is inventor; Orthogenics AS is Applicant).
Gérard HC, Wang Z, Wang GF, El-Gabalawy H, Goldbach-Mansky R, Li Y, Majeed W, Zhang H, Ngai N, Hudson AP, Schumacher HR. (2001) Chromosomal DNA from a variety of bacterial species is present in synovial tissue from patients with various forms of arthritis. Arthritis Rheum. 44(7): 1689-1697.
van der Heijden IM, Wilbrink B, Tchetverikov I, Schrijver IA, Schouls LM, Hazenberg MP, Breedveld FC, Tak PP. (2000) Presence of bacterial DNA and bacterial peptidoglycans in joints of patients with rheumatoid arthritis and other arthritides. Arthritis Rheum. Mar. 2000;43(3): 593-598.
Wilkinson NZ, Kingsley GH, Jones HW, Sieper J, Braun J, Ward ME. (1999) The detection of DNA from a range of bacterial species in the joints of patients with a variety of arthritides using a nested, broad-range polymerase chain reaction. Rheumatology (Oxford). 38(3): 260-266.
Wilbrink B, van der Heijden IM, Schouls LM, van Embden JD, Hazes JM, Breedveld FC, Tak PP. (1988) Detection of bacterial DNA in joint samples from patients with undifferentiated arthritis and reactive arthritis, using polymerase chain reaction with universal 16S ribosomal RNA primers. Arthritis Rheum. 41(3): 535-543.
Response to Final Office Action filed Jan. 27, 2011 for U.S. Appl. 10/480,775, which claims priority to PCT/GB2002/002771 filed on Jun. 17, 2001 (M.R. El-Gewely is inventor).
U.S. Appl. No. 10/480,775, El-Gewely, Jun. 4, 2004, Response to Non-Final Rejection, May 22, 2008.
U.S. Appl. No. 10/480,775, El-Gewely, Jun. 4, 2004, Non-Final Rejection, Jan. 22, 2008.

U.S. Appl. No. 10/480,775, El-Gewely, Jun. 4, 2004, List of references, Jan. 22, 2008.
U.S. Appl. No. 10/480,775, El-Gewely, Jun. 4, 2004, Amendment Submitted/Entered with Filing of CPA/RCE, Oct. 31, 2007.
U.S. Appl. No. 10/480,775, El-Gewely, Jun. 4, 2004, Claims, Oct. 31, 2007.
U.S. Appl. No. 10/480,775, El-Gewely, Jun. 4, 2004, Applicant Arguments/Remarks Made in an Amendment, Oct. 31, 2007.
U.S. Appl. No. 10/480,775, El-Gewely, Jun. 4, 2004, Final Rejection, Jul. 5, 2007.
U.S. Appl. No. 10/480,775, El-Gewely, Jun. 4, 2004, Amendment-After Non-Final Rejection, May 15, 2007.
U.S. Appl. No. 10/480,775, El-Gewely, Jun. 4, 2004, Claims, May 15, 2007.
U.S. Appl. No. 10/480,775, El-Gewely, Jun. 4, 2004, Applicant Arguments/Remarks Made in an Amendment, May 15, 2007.
U.S. Appl. No. 10/480,775, El-Gewely, Jun. 4, 2004, Rule 130, 131 or 132 Affidavits, May 15, 2007.
U.S. Appl. No. 10/480,775, El-Gewely, Jun. 4, 2004, Examiner Interview Summary Record (PTOL-413), Mar. 2, 2007.
U.S. Appl. No. 10/480,775, El-Gewely, Jun. 4, 2004, Examiner's search strategy and results, Feb. 6, 2007.
U.S. Appl. No. 10/480,775, El-Gewely, Jun. 4, 2004, Non-Final Rejection, Nov. 7, 2006.
U.S. Appl. No. 10/480,775, El-Gewely, Jun. 4, 2004, List of references, Nov. 7, 2006.
U.S. Appl. No. 10/480,775, El-Gewely, Jun. 4, 2004, Examiner's search strategy and results, Nov. 3, 2006.
U.S. Appl. No. 10/480,775, El-Gewely, Jun. 4, 2004, Amendment Submitted/Entered with Filing of CPA/RCE, Oct. 20, 2006.
U.S. Appl. No. 10/480,775, El-Gewely, Jun. 4, 2004, Claims, Oct. 20, 2006.
U.S. Appl. No. 10/480,775, El-Gewely, Jun. 4, 2004 Applicant Arguments/Remarks Made in an Amendment, Oct. 20, 2006.
U.S. Appl. No. 10/480,775, El-Gewely, Jun. 4, 2004, Advisory Action (PTOL-303), Aug. 29, 2006.
U.S. Appl. No. 10/480,775, El-Gewely, Jun. 4, 2004, Amendment After Final, Aug. 18, 2006.
U.S. Appl. No. 10/480,775, El-Gewely, Jun. 4, 2004, Claims, Aug. 18, 2006.
U.S. Appl. No. 10/480,775, El-Gewely, Jun. 4, 2004, Applicant Arguments/Remarks Made in an Amendment, Aug. 18, 2006.
U.S. Appl. No. 10/480,775, El-Gewely, Jun. 4, 2004, Examiner Interview Summary Record (PTOL-413) Jul. 26, 2006.
U.S. Appl. No. 10/480,775, El-Gewely, Jun. 4, 2004, Final Rejection, Feb. 16, 2006.
U.S. Appl. No. 10/480,775, El-Gewely, Jun. 4, 2004, List of references, Feb. 16, 2006.
U.S. Appl. No. 10/480,775, El-Gewely, Jun. 4, 2004, Amendment-After Non-Final Rejection, Dec. 30, 2005.
U.S. Appl. No. 10/480,775, El-Gewely, Jun. 4, 2004, Claims, Dec. 30, 2005.
U.S. Appl. No. 10/480,775, El-Gewely, Jun. 4, 2004, Applicant Arguments/Remarks Made in an Amendment, Dec. 30, 2005.
U.S. Appl. No. 10/480,775, El-Gewely, Jun. 4, 2004, Non-Final Rejection Aug. 24, 2005.
U.S. Appl. No. 10/480,775, El-Gewely, Jun. 4, 2004, List of references, Aug. 24, 2005.
U.S. Appl. No. 10/480,775, El-Gewely, Jun. 4, 2004, Response to Election / Restriction Filed, Jun. 29, 2005.
U.S. Appl. No. 10/480,775, El-Gewely, Jun. 4, 2004, Requirement for Restriction/Election, May 27, 2005.
U.S. Appl. No. 10/480,775, El-Gewely, Jun. 4, 2004, Preliminary Amendment, Dec. 15, 2003.
U.S. Appl. No. 10/480,775, El-Gewely, Jun. 4, 2004, Specification, Dec. 15, 2003.
U.S. Appl. No. 10/480,775, El-Gewely, Jun. 4, 2004, Claims, Dec. 15, 2003.
U.S. Appl. No. 10/480,775, El-Gewely, Jun. 4, 2004, Applicant Arguments/Remarks Made in an Amendment, Dec. 15, 2003.
PCT/GB02/02271, El Gewely, Jun. 17, 2002, PCT with International Search Report, Dec. 27, 2002.
PCT/GB02/02271, El Gewely, Jun. 17, 2002, International Preliminary Examination Report, Dec. 15, 2003.
AU20020302833, El-Gewely, Jun. 17, 2002, Notice of Allowance, May 8, 2007.
AU20020302833, El-Gewely, Jun. 17, 2002, Further Exam Report, Mar. 12, 2007.
AU20020302833, El-Gewely, Jun. 17, 2002, Reply to Exam Report (claims which were allowed), Feb. 21, 2007.
AU20020302833, El-Gewely, Jun. 17, 2002, Further Exam Report, Dec. 14, 2006.
AU20020302833, El-Gewely, Jun. 17, 2002, Reply to Exam Report (claims which second Exam Report was based), Nov. 28, 2006.
AU20020302833, El-Gewely, Jun. 17, 2002, First Report Date, Feb. 21, 2006.
AU20020302833, El-Gewely, Jun. 17, 2002, Claims on which the first Exam Report was based).
EP20020730515, El-Gewely, Jun. 17, 2002, Examination report, Dec. 17, 2007.
EP20020730515, El-Gewely, Jun. 17, 2002, Annex to the communication, Dec. 17, 2007.
EP20020730515, El-Gewely, Jun. 17, 2002, Communication regarding possible amendment of claims/payment of claims fees, Feb. 24, 2004.
EP20020730515, El-Gewely, Jun. 17, 2002, Amendments received before examination, Jan. 16, 2004.
EP20020730515, El-Gewely, Jun. 17, 2002, Amended claims filed after receipt of (European) search report, Jan. 16, 2004.
EP20020730515, El-Gewely, Jun. 17, 2002, Annex, Jan. 16, 2004.
EP20020730515, El-Gewely, Jun. 17, 2002, Specification filed by fax and/or in non-official language (no drawings), Jan. 14, 2004.
EP20020730515, El-Gewely, Jun. 17, 2002, Amendments received before examination, Jan. 14, 2004.

* cited by examiner

```
  1  gcgactggaa acCAGAAAAT MCGGCCTTCT GGGARRATAA AGGAARACAT
 51  ATTGCTCGAA GAAATCTCTG GATATCAGTC AGTTGTCTAC TTCTTGCCTT
101  CTGTGTCTGG ATGCTATTTA GCGCAGTTAC CGTTAATCTC AATAAAATCG
151  GTTTTAATTT TACTACCGAT CAACTCTTTT TTATTAACCC TCACTAAAGC
201  ACCGTCCATC GGCGTCCACC GAATATAGGC ACCATAAAGG AGTAGGGAAC
251  ACGCAATAAT GCGCCAGAAA CGGAGGGTAA TGCGGTTAAT AAAAAGAGTT
301  GATCGGTAGT AAAATTAAAA CCGATTTTAT TGAGATTAAC GGTAACTGCG
351  CTAAATAGCA TCCAGACACA GAAGGCAAGA AGTAGACAAC TGACTGATAT
401  CCAGAGATTT CTTCGAGCAA TATGTTTTCC TTTATTTTCC CAGAAGGCCG
451  GATTTTCTGG TTTCCAGTCG CGCAAAAGAT AACGACTATT TTTCTCAtTT
501  TBGCAGTGCC ATATTGTTCC TCACATGCAC ATCATTGGTA ACgaaaaaaa
551  aagatatcac tcagcataat gagaaaaata gtcgttatct tttgcgcgac
601  trgaaaccwk aaaatccggy cttctgggaa watamatgga wavcathttg
651  ctccagaaag tctctggtak cagwctagtb tgmtattcct gashtttctt
```

Fig 6

```
GNGGNNAGTG   NNNGNNTNTN   NTANTNTNNT   NTTGATGCCC   CACCATGCAA
GTCGAACGGC AGCACGGAGC TTGCTCTGGT

GGCGAGTGGC   GAACGGGTGA   GTAATATATC   GGAACGTACC   CTAGAGTGGG
GGATAACGTA GCGAAAGTTA CGCTAATACC

GCATACGATC   TAAGGATGAA   AGTGGGGGAT   CGCAAGACCT   CATGCTCGTG
GAGCGGCCGA TATCTGATTA GCTAGTTGGT

AGGGTAAAAG   CCTACCAAGG   CATCGATCAG   TAGCTGGTCT   GAGAGGACGA
CCAGCCACAC TGGAACTGAG ACACGGTCCA

GACTCCTACG   GGAGGCAGCA   GTGGGGAATT   TTGGACAATG   GGCGAAAGCC
TGATCCAGCA ATGCCGCGTG AGTGAAGAAG

GCCTTCGGGT   TGTAAAGCTC   TTTTGTCAGG   GAAGAAACGG   TGAGAGCTAA
TATCTCTTGC TAATGACGGT ACCTGAAGAA

TAAGCACCGG CTAACTACGT GCCAGCAGCCG CGGTAATAC
GTAGGGTGCA AGCGTTAATC GGAATTACTG GGCGTAAAGC

GTGCGCAGGC GGTTTTGTAA GTCTGATGT GAAATCCCCG
GGCTCAACCT GGGAATTGCA TTGGAGACT GCAAGGCTAG

AATCTGGCAG AGGGGGGTA GAATTCCACG TGTAGCAGTG
AAATGCGTAG ATATGTGGAG GAACACCGAT GGCGAAGGCA

GCCCCCTGGG   TCAAGATTGA   CGCTCATGCA   CGAAAGCGTG   GGGAGCAAAC
AGGATTAGAT ACCCTGGTAG TCCACGCCCT

AAACGATGTC   TACTAGTTGT   CGGGTCTTAA   TTGACTTGGT   AACGCAGCTA
ACGCGTGAAG TAGACCGCCT GGGGAGTACG

GTCGCAAGAT   TAAAACTCAAA   GGAATTGACG   GGGACCCGCA   CAAGCGGTGG
ATGATGTGGA TTAATTCGAT GCAACGCGAA

AAACCTTACC   TACCCTTGAC   ATGGCTGGAA   TCCTTGAGAG   ATCAGGGAGT
GCTCGAAAGA GAACCAGTAC ACAGGTGCTG

CATGGCTGTC   GTCAGCTCGT   GTCGTGAGAT   GTTGGGTTAA   GTCCCGCAAC
GAGCGCAACC CTTGTCATTA GTTGCTACGA

AAGGGCACTC   TAATGAGACT   GCCGGTGACA   AACCGGAGGA   AGGTGGGGAT
GACGTCAAGT CCTCATGGCC CTTATGGGTA
```

Fig 12

```
GGGCTTCACA   CGTCATACAA   TGGTACATAC   AGAGCGCCGC   CAACCCGCGA
GGGGGAGCTA ATCGCAGAAA GTGTATCGTA

GTCCGGATTG   TAGTCTGCAA   CTCGACTGCA   TGAAGTTGGA   ATCGCTAGTA
ATCGCGGATC AGCATGTCNC GGTNAANACG

TTCCCGGGTC   TTGTACACAC   CGCCCGTCAC   ACCATGGGAG   CGGGTTTTAC
CAGAAGTAGG TAGCTTANCC NCAAGGAGGG

CGCTTCCAAG GTATNNATCA AANNNNCNNN NNCNNNCCCC
NNNC
```

Fig. 12 cont

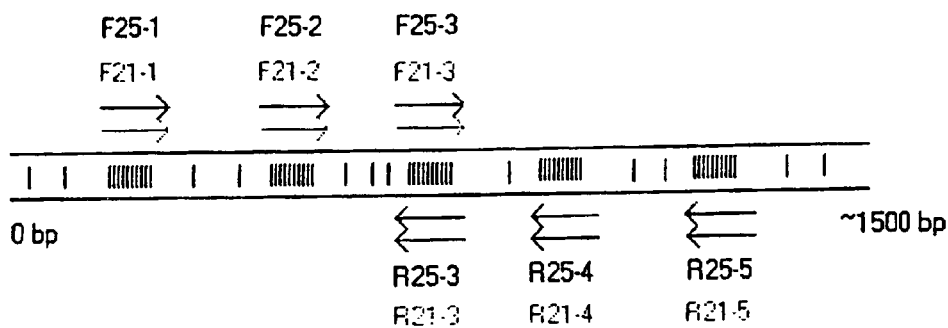

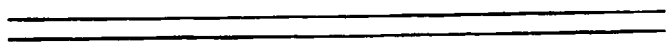

F25-1/R25-5

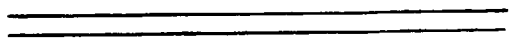

F21-1/R21-4

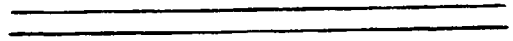

F21-2/R21-5

| ▯▯▯▯ | DNA Region with many a high percentage of mismatch between B- and J-type sequencel |
| --- | --- |
| I | Single basepair mismatch between B- and J-type sequencel |

Fig 13

SEQUENCE LISTING

<160> NUMBER OF SEQ ID NOS: 35

<210> SEQ ID NO 1
<211> LENGTH: 23
<212> TYPE: DNA
<213> ORGANISM: artificial sequence
<220> FEATURE:
<223> OTHER INFORMATION: primer

<400> SEQUENCE: 1
gcaagtcgaa cggcagcacg ggt                                    23

<210> SEQ ID NO 2
<211> LENGTH: 23
<212> TYPE: DNA
<213> ORGANISM: artificial sequence

```
<220> FEATURE:
<223> OTHER INFORMATION: primer

<400> SEQUENCE: 2
ggatagcccg gcgaaagccg gat                                              23

<210> SEQ ID NO 3
<211> LENGTH: 25
<212> TYPE: DNA
<213> ORGANISM: artificial sequence
<220> FEATURE:
<223> OTHER INFORMATION: primer

<400> SEQUENCE: 3
ccttcgggcc tcgcgctata gggtt                                            25

<210> SEQ ID NO 4
<211> LENGTH: 25
<212> TYPE: DNA
<213> ORGANISM: artificial sequence
<220> FEATURE:
<223> OTHER INFORMATION: primer

<400> SEQUENCE: 4
tccttggccc taatacggtc ggggg                                            25

<210> SEQ ID NO 5
<211> LENGTH: 25
<212> TYPE: DNA
<213> ORGANISM: artificial sequence
<220> FEATURE:
<223> OTHER INFORMATION: primer

<400> SEQUENCE: 5
cccccgaccg tattagggcc aagga                                            25

<210> SEQ ID NO 6
<211> LENGTH: 23
<212> TYPE: DNA
<213> ORGANISM: artificial sequence
<220> FEATURE:
<223> OTHER INFORMATION: primer

<400> SEQUENCE: 6
tccacctctc agcggaattc cga                                              23

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
gcaaccctct gttccgacca ttgt                                             24

<210> SEQ ID NO 8
<211> LENGTH: 24
<212> TYPE: DNA
<213> ORGANISM: artificial sequence
<220> FEATURE:
<223> OTHER INFORMATION: primer

<400> SEQUENCE: 8
gattagctcc ccctcgcggg ttgg                                             24
```

```
<210> SEQ ID NO 9
<211> LENGTH: 26
<212> TYPE: DNA
<213> ORGANISM: artificial sequence
<220> FEATURE:
<223> OTHER INFORMATION: primer

<400> SEQUENCE: 9
gggataacgt agcgaaagtt acgcta                                          26

<210> SEQ ID NO 10
<211> LENGTH: 25
<212> TYPE: DNA
<213> ORGANISM: artificial sequence
<220> FEATURE:
<223> OTHER INFORMATION: primer

<400> SEQUENCE: 10
tcgcaagacc tcatgctcgt ggagc                                           25

<210> SEQ ID NO 11
<211> LENGTH: 27
<212> TYPE: DNA
<213> ORGANISM: artificial sequence
<220> FEATURE:
<223> OTHER INFORMATION: primer

<400> SEQUENCE: 11
cggtgagagc taatatctct tgctaat                                         27

<210> SEQ ID NO 12
<211> LENGTH: 27
<212> TYPE: DNA
<213> ORGANISM: artificial sequence
<220> FEATURE:
<223> OTHER INFORMATION: primer

<400> SEQUENCE: 12
attagcaaga gatattagct ctcaccg                                         27

<210> SEQ ID NO 13
<211> LENGTH: 25
<212> TYPE: DNA
<213> ORGANISM: artificial sequence
<220> FEATURE:
<223> OTHER INFORMATION: primer

<400> SEQUENCE: 13
ccctgatctc tcaaggattc cagcc                                           25

<210> SEQ ID NO 14
<211> LENGTH: 27
<212> TYPE: DNA
<213> ORGANISM: artificial sequence
<220> FEATURE:
<223> OTHER INFORMATION: primer

<400> SEQUENCE: 14
gcggcgctct gtatgtacca ttgtatc                                         27

<210> SEQ ID NO 15
<211> LENGTH: 20
<212> TYPE: DNA
<213> ORGANISM: artificial sequence
<220> FEATURE:
<223> OTHER INFORMATION: primer
```

```
<400> SEQUENCE: 15
atcctggctc agattgaacg                                               20

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
tcaccccagt catgaatcct                                               20

<210> SEQ ID NO 17
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: variation
<222> LOCATION: (12)..(12)
<223> OTHER INFORMATION: m= A or C

<400> SEQUENCE: 17
agagtttgat cmtggctcag                                               20

<210> SEQ ID NO 18
<211> LENGTH: 22
<212> TYPE: DNA
<213> ORGANISM: artificial sequence
<220> FEATURE:
<223> OTHER INFORMATION: primer
<220> FEATURE:
<221> NAME/KEY: variation
<222> LOCATION: (6)..(6)
<223> OTHER INFORMATION: Y= T or C

<400> SEQUENCE: 18
tacggytacc ttgttacgac tt                                            22

<210> SEQ ID NO 19
<211> LENGTH: 20
<212> TYPE: DNA
<213> ORGANISM: artificial sequence
<220> FEATURE:
<223> OTHER INFORMATION: primer

<400> SEQUENCE: 19
gtgagtgaag aaggccttcg                                               20

<210> SEQ ID NO 20
<211> LENGTH: 20
<212> TYPE: DNA
<213> ORGANISM: artificial sequence
<220> FEATURE:
<223> OTHER INFORMATION: primer

<400> SEQUENCE: 20
tgggggattc atttccttag                                               20

<210> SEQ ID NO 21
<211> LENGTH: 18
<212> TYPE: DNA
<213> ORGANISM: artificial sequence
<220> FEATURE:
<223> OTHER INFORMATION: primer
```

<400> SEQUENCE: 21
agcagccgcg gtaatacg                                                 18

<210> SEQ ID NO 22
<211> LENGTH: 20
<212> TYPE: DNA
<213> ORGANISM: artificial sequence
<220> FEATURE:
<223> OTHER INFORMATION: primer

<400> SEQUENCE: 22
atgacgtgtg aagccctacc                                               20

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
ttaatccaca tcatccaccg                                               20

<210> SEQ ID NO 24
<211> LENGTH: 18
<212> TYPE: DNA
<213> ORGANISM: artificial sequence
<220> FEATURE:
<223> OTHER INFORMATION: primer

<400> SEQUENCE: 24
agcccgggga tttcacat                                                 18

<210> SEQ ID NO 25
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: variation
<222> LOCATION: (12)..(12)
<223> OTHER INFORMATION: M= C or A

<400> SEQUENCE: 25
agagtttgat cmtgggtcag                                               20

<210> SEQ ID NO 26
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: variation
<222> LOCATION: (16)..(16)
<223> OTHER INFORMATION: Y= T or C

<400> SEQUENCE: 26
agagtttgat cctggytcag                                               20

<210> SEQ ID NO 27
<211> LENGTH: 20
<212> TYPE: DNA
<213> ORGANISM: artificial sequence
<220> FEATURE:
<223> OTHER INFORMATION: primer

```
<220> FEATURE:
<221> NAME/KEY: variation
<222> LOCATION: (12)..(12)
<223> OTHER INFORMATION: R= A or G
<220> FEATURE:
<221> NAME/KEY: variation
<222> LOCATION: (16)..(16)
<223> OTHER INFORMATION: W= A or T

<400> SEQUENCE: 27
ctttacgccc artaawtccg                                         20

<210> SEQ ID NO 28
<211> LENGTH: 700
<212> TYPE: DNA
<213> ORGANISM: unknown
<220> FEATURE:
<223> OTHER INFORMATION: sequence isolated by differential display
<220> FEATURE:
<221> NAME/KEY: variation
<222> LOCATION: (21)..(21)
<223> OTHER INFORMATION: M= A or C
<220> FEATURE:
<221> NAME/KEY: variation
<222> LOCATION: (35)..(36)
<223> OTHER INFORMATION: R= A or G
<220> FEATURE:
<221> NAME/KEY: variation
<222> LOCATION: (46)..(46)
<223> OTHER INFORMATION: R= A or G
<220> FEATURE:
<221> NAME/KEY: variation
<222> LOCATION: (502)..(502)
<223> OTHER INFORMATION: B= G or C or T
<220> FEATURE:
<221> NAME/KEY: variation
<222> LOCATION: (602)..(602)
<223> OTHER INFORMATION: R= A or G
<220> FEATURE:
<221> NAME/KEY: variation
<222> LOCATION: (609)..(609)
<223> OTHER INFORMATION: W= A or T
<220> FEATURE:
<221> NAME/KEY: variation
<222> LOCATION: (610)..(610)
<223> OTHER INFORMATION: K= G or T
<220> FEATURE:
<221> NAME/KEY: variation
<222> LOCATION: (631)..(631)
<223> OTHER INFORMATION: W= A or T
<220> FEATURE:
<221> NAME/KEY: variation
<222> LOCATION: (635)..(635)
<223> OTHER INFORMATION: M= A or C
<220> FEATURE:
<221> NAME/KEY: variation
<222> LOCATION: (641)..(641)
<223> OTHER INFORMATION: W= A or T
<220> FEATURE:
<221> NAME/KEY: variation
<222> LOCATION: (643)..(643)
<223> OTHER INFORMATION: V= G or A or C
<220> FEATURE:
<221> NAME/KEY: variation
<222> LOCATION: (670)..(670)
<223> OTHER INFORMATION: K= G or T
<220> FEATURE:
<221> NAME/KEY: variation
<222> LOCATION: (674)..(674)
<223> OTHER INFORMATION: W= A or T
<220> FEATURE:
<221> NAME/KEY: variation
<222> LOCATION: (680)..(680)
<223> OTHER INFORMATION: B= G or C or T
<220> FEATURE:
<221> NAME/KEY: variation
<222> LOCATION: (680)..(680)
<223> OTHER INFORMATION: Y= T or C
```

<220> FEATURE:
<221> NAME/KEY: variation
<222> LOCATION: (683)..(683)
<223> OTHER INFORMATION: M= A or C
<220> FEATURE:
<221> NAME/KEY: variation
<222> LOCATION: (693)..(693)
<223> OTHER INFORMATION: S = G or C
<220> FEATURE:
<221> NAME/KEY: variation
<222> LOCATION: (694)..(694)
<223> OTHER INFORMATION: H= A or T or C

<400> SEQUENCE: 28

```
gcgactggaa accagaaaat mcggccttct gggarrataa aggaaracat attgctcgaa      60
gaaatctctg gatatcagtc agttgtctac ttcttgcctt ctgtgtctgg atgctattta     120
gcgcagttac cgttaatctc aataaaatcg gttttaattt tactaccgat caactctttt     180
ttattaaccc tcactaaagc accgtccatc ggcgtccacc gaatataggc accataaagg     240
agtagggaac acgcaataat gcgccagaaa cggaggghta tgcggttaat aaaagagtt     300
gatcggtagt aaaattaaaa ccgattttat tgagattaac ggtaactgcg ctaaatagca     360
tccagacaca gaaggcaaga agtagacaac tgactgatat ccagagattt cttcgagcaa     420
tatgttttcc tttattttcc cagaaggccg gattttctgg tttccagtcg cgcaaaagat     480
aacgactatt tttctcattt tbgcagtgcc atattgttcc tcacatgcac atcattggta     540
acgaaaaaaa aagatatcac tcagcataat gagaaaaata gtcgttatct tttgcgcgac     600
trgaaaccwk aaaatccggy cttctgggaa watamatgga wavcathttg ctccagaaag     660
tctctggtak cagwctagtb tgmtattcct gashtttctt                           700
```

<210> SEQ ID NO 29
<211> LENGTH: 1482
<212> TYPE: DNA
<213> ORGANISM: Janthinobacterium
<220> FEATURE:
<221> NAME/KEY: misc_feature
<222> LOCATION: (2)..(2)
<223> OTHER INFORMATION: N= A, C, G or T
<220> FEATURE:
<221> NAME/KEY: misc_feature
<222> LOCATION: (5)..(6)
<223> OTHER INFORMATION: N= A, C, G or T
<220> FEATURE:
<221> NAME/KEY: misc_feature
<222> LOCATION: (11)..(13)
<223> OTHER INFORMATION: N= A, C, G or T
<220> FEATURE:
<221> NAME/KEY: misc_feature
<222> LOCATION: (15)..(16)
<223> OTHER INFORMATION: N= A, C, G or T
<220> FEATURE:
<221> NAME/KEY: misc_feature
<222> LOCATION: (18)..(18)
<223> OTHER INFORMATION: N= A, C, G or T
<220> FEATURE:
<221> NAME/KEY: misc_feature
<222> LOCATION: (20)..(21)
<223> OTHER INFORMATION: N= A, C, G or T
<220> FEATURE:
<221> NAME/KEY: misc_feature
<222> LOCATION: (24)..(24)
<223> OTHER INFORMATION: N= A, C, G or T
<220> FEATURE:
<221> NAME/KEY: misc_feature
<222> LOCATION: (26)..(26)
<223> OTHER INFORMATION: N= A, C, G or T
<220> FEATURE:
<221> NAME/KEY: misc_feature
<222> LOCATION: (28)..(29)
<223> OTHER INFORMATION: N= A, C, G or T

```
<220> FEATURE:
<221> NAME/KEY: misc_feature
<222> LOCATION: (31)..(31)
<223> OTHER INFORMATION: N= A, C, G or T
<220> FEATURE:
<221> NAME/KEY: misc_feature
<222> LOCATION: (1347)..(1347)
<223> OTHER INFORMATION: N= A, C, G or T
<220> FEATURE:
<221> NAME/KEY: misc_feature
<222> LOCATION: (1352)..(1352)
<223> OTHER INFORMATION: N= A, C, G or T
<220> FEATURE:
<221> NAME/KEY: misc_feature
<222> LOCATION: (1355)..(1355)
<223> OTHER INFORMATION: N= A, C, G or T
<220> FEATURE:
<221> NAME/KEY: misc_feature
<222> LOCATION: (1426)..(1426)
<223> OTHER INFORMATION: N= A, C, G or T
<220> FEATURE:
<221> NAME/KEY: misc_feature
<222> LOCATION: (1429)..(1429)
<223> OTHER INFORMATION: N= A, C, G or T
<220> FEATURE:
<221> NAME/KEY: misc_feature
<222> LOCATION: (1453)..(1454)
<223> OTHER INFORMATION: N= A, C, G or T
<220> FEATURE:
<221> NAME/KEY: misc_feature
<222> LOCATION: (1461)..(1464)
<223> OTHER INFORMATION: N= A, C, G or T
<220> FEATURE:
<221> NAME/KEY: misc_feature
<222> LOCATION: (1466)..(1470)
<223> OTHER INFORMATION: N= A, C, G or T
<220> FEATURE:
<221> NAME/KEY: misc_feature
<222> LOCATION: (1472)..(1474)
<223> OTHER INFORMATION: N= A, C, G or T
<220> FEATURE:
<221> NAME/KEY: misc_feature
<222> LOCATION: (1479)..(1481)
<223> OTHER INFORMATION: N= A, C, G or T

<400> SEQUENCE: 29
gnggnnagtg nnngnntntn ntantntnnt nttgatgccc caccatgcaa gtcgaacggc      60
agcacggagc ttgctctggt ggcgagtggc gaacgggtga gtaatatatc ggaacgtacc     120
ctagagtggg ggataacgta gcgaaagtta cgctaatacc gcatacgatc taaggatgaa     180
agtgggggat cgcaagacct catgctcgtg gagcggccga tatctgatta gctagttggt     240
agggtaaaag cctaccaagg catcgatcag tagctggtct gagaggacga ccagccacac     300
tggaactgag acacggtcca gactcctacg ggaggcagca gtggggaatt ttggacaatg     360
ggcgaaagcc tgatccagca atgccgcgtg agtgaagaag ccttcgggt tgtaaagctc     420 ttttgtcagg gaagaaacgg tgagagctaa tatctcttgc taatgacggt acctgaagaa     480
taagcaccgg ctaactacgt gccagcagcc gcggtaatac gtagggtgca agcgttaatc     540
ggaattactg ggcgtaaagc gtgcgcaggc ggttttgtaa gtctgatgtg aaatcccgg      600 gctcaacctg gaattgcat tggagactgc aaggctagaa tctggcagag gggggtagaa     660
ttccacgtgt agcagtgaaa tgcgtagata tgtggaggaa caccgatggc gaaggcagcc     720
ccctgggtca agattgacgc tcatgcacga aagcgtgggg agcaaacagg attagatacc     780
ctggtagtcc acgccctaaa cgatgtctac tagttgtcgg gtcttaattg acttggtaac     840
gcagctaacg cgtgaagtag accgcctggg gagtacggtc gcaagattaa aactcaaagg     900
aattgacggg gacccgcaca agcggtggat gatgtggatt aattcgatgc aacgcgaaaa     960
accttaccta cccttgacat ggctggaatc cttgagagat cagggagtgc tcgaaagaga    1020
```

-continued

| | | | | |
|---|---|---|---|---|
| accagtacac | aggtgctgca | tggctgtcgt | cagctcgtgt | cgtgagatgt | tgggttaagt | 1080 |
| cccgcaacga | gcgcaaccct | tgtcattagt | tgctacgaaa | gggcactcta | atgagactgc | 1140 |
| cggtgacaaa | ccggaggaag | gtggggatga | cgtcaagtcc | tcatggccct | tatgggtagg | 1200 |
| gcttcacacg | tcatacaatg | gtacatacag | agcgccgcca | acccgcgagg | gggagctaat | 1260 |
| cgcagaaagt | gtatcgtagt | ccggattgta | gtctgcaact | cgactgcatg | aagttggaat | 1320 |
| cgctagtaat | cgcggatcag | catgtcncgg | tnaanacgtt | cccgggtctt | gtacacaccg | 1380 |
| cccgtcacac | catgggagcg | gttttacca | gaagtaggta | gcttanccnc | aaggagggcg | 1440 |
| cttccaaggt | atnnatcaaa | nnnncnnnnn | cnnncccnn | nc | | 1482 |

<210> SEQ ID NO 30
<211> LENGTH: 1400
<212> TYPE: DNA
<213> ORGANISM: Duganella

<400> SEQUENCE: 30

| | | | | | | |
|---|---|---|---|---|---|---|
| catgtaagtc | gaacggcagc | acggagcttg | ctctggtggc | gagtggcgaa | cgggtgagta | 60 |
| atatatcgga | acgtaccta | gagtgggga | taacgtagcg | aaagttacgc | taataccgca | 120 |
| tacgatctaa | ggatgaaagt | gggggatcgc | aagacctcat | gctcgtggag | cggccgatat | 180 |
| ctgattagct | agttggtagg | gtaaaagcct | accaaggcat | cgatcagtag | ctggtctgag | 240 |
| aggacgacca | gccacactgg | aactgagaca | cggtccagac | tcctacggga | ggcagcagtg | 300 |
| gggaattttg | gacaatgggc | gaaagcctga | tccagcaatg | ccgcgtgagt | gaagaaggcc | 360 |
| ttcgggttgt | aaagctcttt | tgtcaggaa | gaaacggtga | gagctaatat | ctcttgctaa | 420 |
| tgacggtacc | tgaagaataa | gcaccggcta | actacgtgcc | agcagccgcg | gtaatacgta | 480 |
| gggtgcaagc | gttaatcgga | attactgggc | gtaaagcgtg | cgcaggcggt | tttgtaagtc | 540 |
| tgatgtgaaa | tccccgggct | caacctggga | attgcattgg | agactgcaag | gctagaatct | 600 |
| ggcagagggg | ggtagaattc | cacgtgtagc | agtgaaatgc | gtagatatgt | ggaggaacac | 660 |
| cgatggcgaa | ggcagccccc | tgggtcaaga | ttgacgctca | tgcacgaaag | cgtggggagc | 720 |
| aaacaggatt | agataccctg | gtagtccacg | ccctaaacga | tgtctactag | ttgtcgggtc | 780 |
| ttaattgact | tggtaacgca | gctaacgcgt | gaagtagacc | gcctggggag | tacggtcgca | 840 |
| agattaaaac | tcaaaggaat | tgacggggac | ccgcacaagc | ggtggatgat | gtggattaat | 900 |
| tcgatgcaac | gcgaaaaacc | ttacctaccc | ttgacatggc | tggaatcctt | gagagatcag | 960 |
| ggagtgctcg | aaagagaacc | agtacacagg | tgctgcatgg | ctgtcgtcag | ctcgtgtcgt | 1020 |
| gagatgttgg | gttaagtccc | gcaacgagcg | caacccttgt | cattagttgc | tacgaaaggg | 1080 |
| cactctaatg | agactgccgg | tgacaaaccg | gaggaaggtg | gggatgacgt | caagtcctca | 1140 |
| tggcccttat | gggtagggct | tcacacgtca | tacaatggta | catacagagc | gccgccaacc | 1200 |
| cgcgaggggg | agctaatcgc | agaaagtgta | tcgtagtccg | gattgtagtc | tgcaactcga | 1260 |
| ctgcatgaag | ttggaatcgc | tagtaatcgc | ggatcagcat | gtcgcggtga | atacgttccc | 1320 |
| gggtcttgta | cacaccgccc | gtcacaccat | gggagcgggt | tttaccagaa | gtaggtagct | 1380 |
| taaccgtaag | gagggcgctt | | | | | 1400 |

<210> SEQ ID NO 31
<211> LENGTH: 1400
<212> TYPE: DNA
<213> ORGANISM: Janthinobacterium

```
<220> FEATURE:
<221> NAME/KEY: misc_feature
<222> LOCATION: (1304)..(1304)
<223> OTHER INFORMATION: N= A, C, G or T
<220> FEATURE:
<221> NAME/KEY: misc_feature
<222> LOCATION: (1309)..(1309)
<223> OTHER INFORMATION: N= A, C, G or T
<220> FEATURE:
<221> NAME/KEY: misc_feature
<222> LOCATION: (1312)..(1312)
<223> OTHER INFORMATION: N= A, C, G or T
<220> FEATURE:
<221> NAME/KEY: misc_feature
<222> LOCATION: (1383)..(1383)
<223> OTHER INFORMATION: N= A, C, G or T
<220> FEATURE:
<221> NAME/KEY: misc_feature
<222> LOCATION: (1386)..(1386)
<223> OTHER INFORMATION: N= A, C, G or T

<400> SEQUENCE: 31
catgcaagtc gaacggcagc acggagcttg ctctggtggc gagtggcgaa cgggtgagta      60
atatatcgga acgtaccta  gagtgggga  taacgtagcg aaagttacgc taataccgca     120
tacgatctaa ggatgaaagt gggggatcgc aagacctcat gctcgtggag cggccgatat     180
ctgattagct agttggtagg gtaaaagcct accaaggcat cgatcagtag ctggtctgag     240
aggacgacca gccacactgg aactgagaca cggtccagac tcctacggga ggcagcagtg     300
gggaattttg gacaatgggc gaaagcctga tccagcaatg ccgcgtgagt gaagaaggcc     360
ttcgggttgt aaagctcttt tgtcagggaa gaaacggtga gagctaatat ctcttgctaa     420
tgacggtacc tgaagaataa gcaccggcta actacgtgcc agcagccgcg gtaatacgta     480
gggtgcaagc gttaatcgga attactgggc gtaaagcgtg cgcaggcggt tttgtaagtc     540
tgatgtgaaa tccccgggct caacctggga attgcattgg agactgcaag gctagaatct     600
ggcagagggg ggtagaattc cacgtgtagc agtgaaatgc gtagatatgt ggaggaacac     660
cgatggcgaa ggcagccccc tgggtcaaga ttgacgctca tgcacgaaag cgtggggagc     720
aaacaggatt agataccctg gtagtccacg ccctaaacga tgtctactag ttgtcgggtc     780
ttaattgact tggtaacgca gctaacgcgt gaagtagacc gcctggggag tacggtcgca     840
agattaaaac tcaaaggaat tgacggggac ccgcacaagc ggtggatgat gtggattaat     900
tcgatgcaac gcgaaaaacc ttacctaccc ttgacatggc tggaatcctt gagagatcag     960
ggagtgctcg aaagagaacc agtacacagg tgctgcatgg ctgtcgtcag ctcgtgtcgt    1020
gagatgttgg gttaagtccc gcaacgagcg caacccttgt cattagttgc tacgaaaggg    1080
cactctaatg agactgccgg tgacaaaccg gaggaaggtg gggatgacgt caagtcctca    1140
tggcccttat gggtagggct tcacacgtca tacaatggta catacagagc gccgccaacc    1200
cgcgaggggg agctaatcgc agaaagtgta tcgtagtccg gattgtagtc tgcaactcga    1260
ctgcatgaag ttggaatcgc tagtaatcgc ggatcagcat gtcncggtna anacgttccc    1320
gggtcttgta cacaccgccc gtcacaccat gggagcgggt tttaccagaa gtaggtagct    1380
tanccncaag gagggcgctt                                                1400

<210> SEQ ID NO 32
<211> LENGTH: 1400
<212> TYPE: DNA
<213> ORGANISM: Janthinobacterium
```

<400> SEQUENCE: 32

```
catgcaagtc gaacggcagc acggagcttg ctctggtggc gagtggcgaa cgggtgagta      60
atatatcgga acgtacccta gagtggggga taacgtagcg aaagttacgc taataccgca     120
tacgatctaa ggatgaaagt gggggatcgc aagacctcat gctcgtggag cggccgatat     180
ctgattagct agttggtagg gtaaaagcct accaaggcat cgatcagtag ctggtctgag     240
aggacgacca gccacactgg aactgagaca cggtccagac tcctacggga ggcagcagtg     300
gggaattttg gacaatgggc gaaagcctga tccagcaatg ccgcgtgagt gaagaaggcc     360
ttcgggttgt aaagctcttt tgtcagggaa gaaacggtga gagctaatat ctcttgctaa     420
tgacggtacc tgaagaataa gcaccggcta actacgtgcc agcagccgcg gtaatacgta     480
gggtgcaagc gttaatcgga attactgggc gtaaagcgtg cgcaggcggt tttgtaagtc     540
tgatgtgaaa tccccgggct caacctggga attgcattgg agactgcaag gctagaatct     600
ggcagagggg ggtagaattc cacgtgtagc agtgaaatgc gtagatatgt ggaggaacac     660
cgatggcgaa ggcagcccccc tgggtcaaga ttgacgctca tgcacgaaag cgtggggagc     720
aaacaggatt agataccctg gtagtccacg ccctaaacga tgtctactag ttgtcgggtc     780
ttaattgact tggtaacgca gctaacgcgt gaagtagacc gcctggggag tacggtcgca     840
agattaaaac tcaaaggaat tgacgggggac ccgcacaagc ggtggatgat gtggattaat     900
tcgatgcaac gcgaaaaacc ttacctaccc ttgacatggc tggaatcctc gagagattga     960
ggagtgctcg aaagagaacc agtacacagg tgctgcatgg ctgtcgtcag ctcgtgtcgt    1020
gagatgttgg gttaagtccc gcaacgagcg caacccttgt cattagttgc tacgaaaggg    1080
cactctaatg agactgccgg tgacaaaccg gaggaaggtg gggatgacgt caagtcctca    1140
tggcccttat gggtagggct tcacacgtca tacaatggta catacagagc gccgccaacc    1200
cgcgaggggg agctaatcgc agaaagtgta tcgtagtccg gattgtagtc tgcaactcga    1260
ctgcatgaag ttggaatcgc tagtaatcgc ggatcagcat gtcgcggtga atacgttccc    1320
gggtcttgta cacaccgccc gtcacaccat gggagcgggt tttaccagaa gtaggtagct    1380
taaccgcaag gagggcgctt                                                1400
```

<210> SEQ ID NO 33
<211> LENGTH: 1400
<212> TYPE: DNA
<213> ORGANISM: Janthinobacterium lividum

<400> SEQUENCE: 33

```
catgcaagtc gaacggcagc acggagcttg ctctggtggc gagtggcgaa cgggtgagta      60
atatatcgga acgtacccta gagtggggga taacgtagcg aaagttacgc taataccgca     120
tacgatctaa ggatgaaagt gggggatcgc aagacctcat gctcgtggag cggccgatat     180
ctgattagct agttggtagg gtaaaagcct accaaggcat cgatcagtag ctggtctgag     240
aggacgacca gccacactgg aactgagaca cggtccagac tcctacggga ggcagcagtg     300
gggaattttg gacaatgggc gaaagcctga tccagcaatg ccgcgtgagt gaagaaggcc     360
ttcgggttgt aaagctcttt tgtcagggaa gaaacggtga gagctaatat ctcttgctaa     420
tgacggtacc tgaagaataa gcaccggcta actacgtgcc agcagccgcg gtaatacgta     480
gggtgcaagc gttaatcgga attactgggc gtaaagcgtg cgcaggcggt tttgtaagtc     540
tgatgtgaaa tccccgggct caacctggga attgcattgg agactgcaag gctagaatct     600
ggcagagggg ggtagaattc cacgtgtagc agtgaaatgc gtagatatgt ggaggaacac     660
```

-continued

```
cgatggcgaa ggcagccccc tgggtcaaga ttgacgctca tgcacgaaag cgtggggagc      720
aaacaggatt agatacectg gtagtccacg ccctaaacga tgtctactag ttgtcgggtc      780
ttaattgact tggtaacgca gctaacgcgt gaagtagacc gcctggggag tacggtcgca      840
agattaaaac tcaaaggaat tgacggggac ccgcacaagc ggtggatgat gtggattaat      900
tcgatgcaac gcgaaaaacc ttacctaccc ttgacatggc tggaatcccc gagagattgg      960
ggagtgctcg aaagagaacc agtacacagg tgctgcatgg ctgtcgtcag ctcgtgtcgt     1020
gagatgttgg gttaagtccc gcaacgagcg caacccttgt cattagttgc tacgaaaggg     1080
cactctaatg agactgccgg tgacaaaccg gaggaaggtg gggatgacgt caagtcctca     1140
tggcccttat gggtagggct tcacacgtca tacaatggta catacagagc gccgccaacc     1200 cgcgagggg agctaatcgc agaaagtgta tcgtagtccg gattgtagtc tgcaactcga     1260
ctgcatgaag ttggaatcgc tagtaatcgc ggatcagcat gtcgcggtga atacgttccc     1320
gggtcttgta cacaccgccc gtcacaccat gggagcgggt tttaccagaa gtaggtagct     1380
taaccgcaag gagggcgctt                                                 1400
```

<210> SEQ ID NO 34
<211> LENGTH: 688
<212> TYPE: DNA
<213> ORGANISM: Janthinobacterium lividum

<400> SEQUENCE: 34

```
gagcttgctc tggtggcgag tggcgaacgg gtgagtaata tatcggaacg tacectagag       60 tgggggataa cgtagcgaaa gttacgctaa taccgcatac gatctaagga tgaaagtggg      120
ggatcgcaag accctcatgct cgtggagcgg ccgatatctg attagctagt tggtagggta      180
aaagcctacc aaggcatcga tcagtagctg gtctgagagg acgaccagcc acactggaac      240
tgagacacgg tccagactcc tacgggaggc agcagtgggg aattttggac aatgggcgaa      300
agcctgatcc agcaatgccg cgtgagtgaa gaaggccttc gggttgtaaa gctcttttgt      360
cagggaagaa acggtgagag ctaatatctc ttgctaatga cggtacctga agaataagca      420
ccggctaact acgtgccagc agccgcggta atacgtaggg tgcaagcgtt aatcggaatt      480
actgggcgta aagcgtgcgc aggcggtttt gtaagtctga tgtgaaatcc ccgggctcaa      540
cctgggaatt gcattggaga ctgcaaggct agaatctggc agagggggggt agaattccac      600 gtgtagcagt gaaatgcgta gatatgtgga ggaacaccga tggcgaaggc agccccctgg      660
gtcaagattg acgctcatgc acgaaagc                                        688
```

<210> SEQ ID NO 35
<211> LENGTH: 687
<212> TYPE: DNA
<213> ORGANISM: Janthinobacterium
<220> FEATURE:
<221> NAME/KEY: misc_feature
<222> LOCATION: (1)..(687)
<223> OTHER INFORMATION: S = G or C
<220> FEATURE:
<221> NAME/KEY: misc_feature
<222> LOCATION: (610)..(610)
<223> OTHER INFORMATION: R = A or G
<220> FEATURE:
<221> NAME/KEY: misc_feature
<222> LOCATION: (649)..(649)
<223> OTHER INFORMATION: V = G or A or C
<220> FEATURE:
<221> NAME/KEY: misc_feature
<222> LOCATION: (667)..(667)
<223> OTHER INFORMATION: W = A or T

```
<400> SEQUENCE: 35
gagcttgctc tggtggcgag tggcgaacgg gtgagtaata tatcggaacg taccctagag      60
tgggggataa cgtagcgaaa gttacgctaa taccgcatac gatctaagga tgaaagtggg     120
ggatcgcaag acctcatgct cgtggagcgg ccgatatctg attagctagt tggtagggta     180
aaagcctacc aaggcatcga tcagtagctg gtctgagagg acgaccagcc acactggaac     240
tgagacacgg tccagactcc tacgggaggc agcagtgggg aattttggac aatgggcgaa     300
actgaatcca gcaatgccgc gtgagtgaag aaggccttcg ggttgtaaag ctcttttgtc     360
agggaagaaa cggtgagagc taatatctct tgctaatgac ggtacctgaa gaataagcac     420
cggctaacta cgtgccagca gccgcggtaa tacgtagggt gcaagcgtta atcggaatta     480
ctgggcgtaa agcgtgcgca ggcggttttg taagtctgat gtgaaatccc cgggctcaac     540
ctgggaattg cattggagac tgcaaggcta gaatctggca gagggggta gaattccacg      600 tgtagcagtr aaatgcgtag atatgtggag gaacaccgat ggcgaagsva gccccctggg     660
tcaagawtga cgctcatgca caaaagc                                         687
```

ANTIBACTERIAL TREATMENT OF OSTEOARTHRITIS

CROSS REFERENCE TO RELATED APPLICATIONS

This application is a divisional application of and claims the benefit of U.S. application Ser. No. 10/480,775, filed Jun. 4, 2004, which claims the benefit of U.S. National Phase PCT/GB02/02771, filed Dec. 15, 2003, which claims priority to U.K. Application No. GB 0114672.9, filed Jun. 15, 2001, which applications are incorporated herein fully by this reference.

The present invention relates to osteoarthritis and methods for the treatment and diagnosis thereof.

Osteoarthritis is also known as 'degenerative joint disease' and is the most common type of arthritis, affecting an estimated 20.7 million adults in the United States of America alone (data from www.nih.gov/niams/healthinfo/artrheu.htm). Osteoarthritis primarily affects cartilage, the tissue that cushions the ends of bones within a joint. Osteoarthritis occurs when cartilage begins to fray, wear, and decay. In extreme cases, the cartilage may wear away leaving a bone-on-bone joint. Osteoarthritis (OA) can cause joint pain, reduced joint mobility and disability. Disability results most often when the disease affects the spine and the weight-bearing joints (the knees and hips).

Typically, the symptoms of OA develop rather slowly. A particular joint may ache or be sore after prolonged use or after a period of inactivity, e.g. sleeping. The pain, stiffness and soreness will generally get worse with time and the range of motion at the joint may become reduced. A grating sound on movement indicates that the cartilage in the joint has worn away and the bones are rubbing against each other.

Osteoarthritis is known as 'degenerative arthritis' and it may affect the knee, hip, spine and other structures; it is the most common of all human joint disorders. OA is classified as a non-inflammatory arthritis and thus can be distinguished from rheumatic diseases like rheumatoid arthritis which is classified as an inflammatory arthritis. Rheumatoid arthritis is an inflammatory disease of the lining of the joint (synovium), it is associated with swelling and inflammation of certain joints, muscle pain and eventually the loss of use of the joint altogether. The inflammation tends to be symmetrical which helps in the diagnosis of rheumatoid arthritis. Other diseases within the group of rheumatic diseases include gout which most commonly affects the big toe and develops quickly, infectious arthritis which is a general term used to describe the various forms of arthritis caused by infectious agents such as bacteria or viruses, and reactive arthritis which develops after an infection involving the urinary tract, bowel and other organs and is often associated with eye problems, skin rashes and mouth sores.

The term 'arthritis' is sometimes used to refer to all rheumatic diseases, however the word literally means joint inflammation, i.e. swelling, redness, heat and pain caused by tissue injury or disease in the joint. The different types of arthritis comprise just a part of the rheumatic diseases which also includes diseases described as 'connective tissue diseases' and autoimmune diseases such as fibromyalgia and systemic lupus erythematosus. As discussed above, OA is no longer seen as part of this group as it is a non-inflammatory arthritis.

The cause of OA is not known but it is believed that it results from a combination of factors. It has been thought that increasing age, a family history of the disease, overuse or abuse of a particular joint, injury, being overweight and other diseases may all contribute to the development of OA. The cause or causes of types of infectious arthritis (bacteria and viruses) and gout (uric acid crystals in the joint) are better understood by scientists and clinicians.

The role of certain endogenously produced enzymes in the breakdown of joint cartilage in OA and the possibility of using drugs that block the action of these enzymes has been investigated. In particular, nitric oxide, which is produced by a family of enzymes called nitric oxide synthases, is spontaneously released from human cartilage affected by OA in quantities sufficient to cause cartilage damage. There is a hypothesis that NO inhibits matrix production by interfering with important autocrine and paracrine factors and NO has been shown to inhibit the production of TGF-$\beta$. Activated articular chondrocytes produce large amounts of NO, and there is increasing evidence that this could be involved in the ethiopathogenesis of osteoarthritis. Because of its short half-life, the biological effects of endogenously produced NO are likely to occur locally within the cartilage. (R. Studer, Osteoarthritis and Cartilage Vol. 7, No 4, July 1999). Also, an important component of cartilage is Type II collagen which is degraded by the endogenous metaloproteinase, gelatinase.

Diagnosing rheumatic diseases or OA can be difficult because some symptoms are common to many different diseases. Diagnosis may require referral to a rheumatologist, as even if diagnosis of one of the rheumatic diseases has been made, it may require a specialist to determine which one.

Typically, a diagnosis will require a full review of the patient's medical history including family history, a physical examination, laboratory tests and X-ray or other imaging techniques. The physical examination will typically include investigation of all joints for redress, warmth, deformity, ease of movement and tenderness. As some forms of arthritis, such as lupus, may affect other organs, a complete physical examination including the heart, lungs, abdomen, nervous system, eyes, ears and throat may be necessary. Blood, urine and/or synovial fluid may be needed to perform one of a number of laboratory tests including: for antinuclear antibody, complete blood count, a hematocrit, for rheumatoid factor and urinalysis.

The doctor may need to see the patient more than once in order to make the diagnosis and the final decision will generally be a working diagnosis based on a number of different parameters which relies on the competence and relevant experience of the examining practitioner. A less subjective test for OA which was quick and easy to perform would greatly improve the diagnostic process. As OA is common, it would be useful to identify OA positively but equally if OA could be ruled out at an early stage, this would also be of considerable benefit to the practitioner.

So far as currently available treatments for OA are concerned, there is no single, successful treatment available for all patients. A typical treatment plan usually combines several types of treatment depending on the stage and severity of the condition and the medical and lifestyle needs of the patient. Treatments may include rest and relaxation, exercise, diet changes and medication, in severe cases surgery may be necessary.

It is generally acknowledged (www.nih.gob/niams/healthinfo/artrheu.htm) that available medications used to treat most rheumatic diseases and OA do not provide a cure but rather limit the symptoms of the disease. Although infectious arthritis (e.g. Lyme disease), if diagnosed in time, can be successfully treated with antibiotics.

Medications commonly used to treat OA provide relief from pain. Suitable analgesics include aspirin and other non-steroidal anti-inflammatory drugs (NSAID's) such as ibuprofen, (which have the added benefit of decreasing the inflammation associated with tissue damage). In recent years, early changes in joints have been surgically treated by using a combination of cultivated cartilage cells and periostal covering from the patient, in an attempt to repair the damaged cartilage. Only a small number of patients can be treated by this expensive and invasive method.

It has been postulated (Amin, A. R. et al. (1996) Proc. Natl. Acad. Sci. USA; 93, pp 14014-14019) that tetracyclines could be used in the treatment of OA because of their ability to inhibit the expression of endogenous nitric oxide synthase (NOS). The possibility of using the tetracycline doxycline in the treatment of OA because of its ability to inhibit the patient's collagenase activity was discussed by Yu, L. P. et al. (1991) in J. Rheumatol; 18, pp 1450-2. No product based on these compounds has yet made it on to the market.

It is clear from the above discussion that existing methods for the diagnosis and treatment of OA are not fully satisfactory. Given the number of sufferers of OA, particularly in the ageing western populations, there is a real need for quick and reliable diagnosis of OA and for improved treatments therefor. Following on from a new and surprising discovery, the present invention provides teaching which address both of these problems.

The present inventor has, for the first time, established a link between bacteria and osteoarthritis. It has never before been suggested that bacteria could have a primary role in OA and identification of this role opens up the possibility for a variety of new therapeutic and diagnostic techniques in the field of OA care. According to one aspect, the present invention therefore provides the use of an antibacterial agent in the manufacture of a medicament for the treatment of OA, more particularly for the treatment of a bacterial infection which is responsible for OA. Alternatively expressed, the present invention provides an antibacterial agent for use in the treatment of OA, more particularly for use in the treatment of a bacterial infection which is responsible for OA.

The symptoms and diagnosis of OA are discussed above and although it may be a complex process, a suitably experienced practitioner is usually able to diagnose OA successfully. A useful definition of OA for the purposes of the present invention is as follows: pain in one or more joints, gradual wear of the cartilage in that joint (typically over several years), plus no signs of arthritic changes as are found, for example in rheumatoid arthritis.

Typical changes found in x-ray pictures from patients with OA include a narrow joint space and subchondrial sclerosis. OA is characterised by joint pain and loss of function caused by a generally progressive loss of articular cartilage, followed by attempted repair of the articular cartilage and also remodelling and sclerosis of subchondral bone. Subchondral bone cysts and osteophytes and secondary synovitis inside the joint may also be found. In contrast with the rheumatic diseases, inflammation is not a main aspect of the disease.

OA may be divided into primary and secondary OA, the present invention being of use in the treatment and diagnosis of both forms, particularly primary osteoarthritis. Primary OA is the more common form and occurs with increasing prevalence with increasing age, there is no currently available cure. A definition of primary OA is provided by the American College of Rheumatology (ACR) http://www.rheumatology.org/patients/factsheets.html as follows: OA is a heterogenous group of conditions that lead to joint symptoms and signs that are associated with defective integrity of articulate cartilage, in addition to related changes in the underlying bone and joint margins. Diagnosis will typically involve assessment of pathological, radiographical and clinical aspects.

Secondary OA is less common and causes include metabolic, developmental and genetic abnormalities of articular cartilage. In secondary OA a clear causal condition, event or disease is recognised. Secondary OA often occurs in the following circumstances Stickler's Syndrome (progressive Hereditary Arthro-opthalmopathy), hemochromatosis, calcium pyrophosphate deposition disease, articular surface injury, joint instability, joint incongruity, denervation (Charcot Joint), epiphyseal dysplasias, following septic arthritis (infection), osteonecrosis, osteochondritis dissecans and years after menisceal damage and/or menisceal removal.

In fact, the data presented herein regarding the role of bacterial infection in the development of OA could lead to its classification as a secondary condition, resulting from initial bacterial infection.

As discussed above, the present invention provides medicaments for use in the treatment of bacterial infections responsible for OA. The inventors are the first to identify a primary (i.e. causal) role for bacteria in OA, i.e. infection may be a primary event or secondary to an initiating event in OA but is nevertheless responsible for one or more (typically most or all) of the characteristic symptoms of OA and/or for exacerbating such symptoms. The term 'responsible for' should therefore be interpreted with this relationship in mind.

The clinical data presented herein regarding the treatment of osteoarthritic patients with an antibiotic confirms the molecular data and demonstrates a role for bacteria in osteoarthritis. The majority of patients tested were considered to show improved symptoms following just 4 weeks of treatment with an antibiotic.

Although not wishing to be bound by theory, it seems likely that there may be some initial damage to the cartilage and the OA-causing infection is transmitted through the synovial fluid or through blood vessels developed around the injured cartilage. This active role for bacteria in the development of OA can be contrasted with secondary bacterial infections that may occur e.g. post surgery and are not themselves responsible for the symptoms of OA.

For example, antibiotics have been described previously in a prophylactic context (Espehaug, B. et al. (1997) J. Bone Joint Surg. Br. July; 79(4) pp 590-5). In this study antibiotic-containing cement and/or systemic antibiotics were given to osteoarthritic patients who had just received primary cemented total hip replacements. Implanting metal during the treatment of fractures or OA means increasing the risk of infection as bacteria may easily cruciate the area around a metal implant. The use of antibiotics in this context is not, however, for the treatment of a bacterial infection having a causal role in OA itself. By contrast, according to the present invention, the treatments is typically not prophylactic, i.e. an established infection which is responsible for the observed OA is treated. In addition, the particular bacteria which may cause post-operative problems are different from those now identified to have a causal role in OA and the symptoms thereof.

The present invention can also be distinguished over publications such as Amin et al. (supra) which suggest a possible role for tetracyclines in the treatment of OA through the ability of such molecules to inhibit endogenous enzymes including NOS and collagenase. Clearly, such documents are not concerned with and do not describe the use of tetracyclines in the treatment of a bacterial infection, their antibiotic activity being incidental to the activities of interest. There is no suggestion in these documents of a causal role for bacteria in OA.

The inventors have been able to make the link between bacteria and OA through a series of experiments. Previously, no bacteria have been found in joints with primary osteoarthritis (except in cases with exchange surgery after loosening). As discussed above, sceptic (infectious) arthritis is a different condition and bacteria such as *Streptococcus* and *Staphylococcus* and some gram negative species are normally found in such joints. Only a fortuitous combination of techniques, namely the manner of biopsy taking, modified differential display methods and finally 16s rRNA analysis alerted the inventors to the possibility of bacterial involvement and then confirmed it. It is postulated that the presence of bacteria may have been 'hidden' in the past because the relevant bacteria are difficult to grow in standard culture tests.

The patients included in the "osteoarthritic" group were all going through arthroplasty procedures in a knee. The biopsies were taken during surgery when the joint was being replaced both on the femoral and tibial side. The diagnosis of osteoarthritis was based on pain in the joint, a typical gradual wear of the cartilage for years, no signs of arthritic changes as found in rheumatoid arthritis, and typical changes found on x-ray pictures like a narrow joint space and subchondral sclerosis. The pathological changes were far advanced; this is supported by the need for the patients to undergo joint arthroplasty.

One of the control groups included were patients with normal cartilage, from whom samples were taken during replacement of the anterior cruciate ligament. No recent trauma had disturbed the knees undergoing this operation and the piece of cartilage studied had to be removed during the replacement procedure to allow enough space for the repaired ligament to function. None of these control patients were found to have the identifying bacterial gene sequence.

In the other control group, patients had only localized damaged areas with no general damage to the joint. All were operated on in an attempt to regain the architecture and functions of normal cartilage. This operation included the use of in vitro grown chondrocytes, removal of the damaged cartilage and the covering of the area to be repaired with periosteum and the in vitro grown cells. None of the patients with this limited damage of cartilage were found to have the bacterial gene. These results suggest that in very early stages of OA development there may be little or no bacterial involvement but that a bacterial infection is responsible for the development of full-blown OA and for the advanced and more serious symptoms thereof. It is the progression to full-blown (advanced stage) OA at a given joint which is responsible for the pain and lack of mobility experienced by most patients with OA and therefore treatments which prevent or slow this progression would be desirable.

Symptoms characteristic of early stage OA include pain during activity and a reduced level of activity. At an advanced stage of OA, pain may be observed at rest and at night, as well as during activity. Activity is very reduced and the use of crutches is common. Also associated with advanced OA are reduced movement of the joint and stiffness in the joint.

From the clinician's point of view, in the early stages of OA, joint line pain is found and there may be increased synovial fluid in the joint. Radiographs generally indicate a narrowing of the joint space because the cartilage is reduced. However, MRI scans are more useful than x-ray images in the early stages as they can identify early changes in the cartilage and subchondral bone. Arthroscopy may reveal fibrillation, cracks and defects in the cartilage. In advanced OA, there is increased joint line pain, palpation of osteophytes and usually increased synovial fluid. Radiographs reveal a significant narrowing of the joint space to the joint where it appears like bone on bone with no space for cartilage. X-ray also reveals sclerosis and cysts in the subcondral bone, possible deformation of the joint and usually osteophytes around the joint margins. Arthroscopy reveals absent and degraded cartilage.

Thus, in a further aspect, the present invention provides the use of an antibacterial agent in the manufacture of a medicament for preventing or reducing the development of, or progression to, advanced stage osteoarthritis. If OA is diagnosed at a very early stage, then prophylactic treatment with an antibiotic may be appropriate. Alternatively expressed, the invention provides an antibacterial agent for use in preventing or reducing the development of, or progression to, advanced stage osteoarthritis.

A modified differential display technique was used which is described in detail in the Examples section herein. Differential display is a method which is used to discover genes that are differentially expressed in one situation compared to another. mRNA is reverse transcribed and from the cDNA population a small number of genes are amplified using selected primers and PCR. Separation of the samples under investigation (amplified with the same primer sets) side by side on a high resolution gel yields a pattern of bands, each representing one expressed gene in the original samples. A gene/band that is found in one sample but not in another is said to be differentially expressed.

In this case, biopsies were taken from the knee, in OA patients from the osteoarthritic part of the cartilage and from another patient during repair of the cruciate ligament. In one patient with OA, biopsies from both the osteoarthritic area and an undisturbed area were compared. There was a problem with insufficient mRNA in the cartilage sample. Cartilage tissue is built up of chondrocyte cells surrounded by extracellular matrix. The total number of cells per gram of tissue is low. The extracellular matrix consists mainly of collagen (type II, IX, XI), proteoglycans (aggrecan) and other large molecules such as hyaluronan. Extracting mRNA from small cartilage samples yields almost undetectable levels of mRNA. This is both due to the low number of cells in a small piece of tissue with few cells per weight unit and to the effect of the extracellular matrix on the efficiency of the mRNA extractions/isolation. Proteoglycans readily bind to RNA and thus lowers the yield. Therefore the complete cDNA population was amplified as a preliminary step after reverse transcription.

The differentially expressed bands on the gel can be cut out, reamplified, cloned and then sequenced. This work identified NOS as more highly expressed in osteoarthritic cartilage and sequence analysis indicated that the gene had a greater homology with a bacterial sequence than a human sequence. The presence of bacteria was then confirmed by detecting 16S rRNA in osteoarthritic tissues, indicative of pathogenic bacteria in the affected cartilage tissue.

Further sequencing and comparative studies of the 16S rRNA has enabled identification of the bacterial species involved in OA, and this will allow selection of the most appropriate antibiotics. The species concerned is or is very closely related to *Janthinobacterium*. *Duganella* is an example of a species very closely related to *Janthinobacterium*. The sequence data indicates that the responsible bacteria is related to *Pseudomonas* sub-species. Such bacteria are different from the bacteria which cause problems in hospitals due to infection of wounds and surgical sites. There may be a heterogeneous bacterial population causing OA in the joint(s) of some patients.

By 'antibacterial agent' is meant any compound or formulation which kills bacteria, prevents or inhibits proliferation of bacteria or otherwise weakens or disables bacteria. Both bactericidal and bacteriostatic agents may be used. The agent may have a specific activity for only one or a small number of bacterial species or it may be active against a broad range of bacteria, such as bacterial membrane affecting peptides.

Suitable antibacterial agents can be used locally or administered intravenously or orally. Treatment could include one or more of the following:

a - A small arthroscopy operation that will include flushing through the joint and injecting the selected antibiotic, or an arthrotomy with a needle injecting the selected antibiotic.

b - Again by arthroscopy, placing antibiotic-releasing matrix into affected joints.

c - Oral administration of a selected antibiotic combination.

d - Intravenous administration of a selected antibiotic combination.

Also, prosthesis or cells could be impregnated or formulated with antibiotics before implantation.

Many antibacterial agents are known and more are being developed all the time. Preferred antibacterial agents are those which are effective in the treatment of *Pseudomonas* infections. Antibiotics which are active even against bacterial species which have a tendency to form biofilms by quorum sensing are preferred, as *Pseudomonas, Janthinobacterium* and *Burkholderia* have a high tendency to form such biofilms. Thus, a preferred class of antibiotics are those which are targeted/against the genes or gene products involved in quorum sensing and biofilm formation.

Indeed, it has recently been shown that a major component in bio-films produced by *Pseudomonas* is DNA (the bacteria believed to be responsible for osteoarthritis are similar to *Pseudomonas*). Therefore in a preferred embodiment of the present invention, treatment will be a combined therapy where an antibiotic is co-administered with an agent which can break down DNA, preferably an enzyme e.g. a restriction enzyme or DNase I. A synergistic effect occurs as the enzyme or other agent breaks down the DNA and reduces the viscosity of the bio-film enabling more effective penetration of the antibiotic. Anti-DNA agents such as DNase I will preferably be injected into the affected joint.

The following are specific examples of suitable antibacterial agents: clariththromycin/levofloxacin combination, mercaptoethylguanidine (has been found to inhibit the inflammatory response of *Pseudomonas* infection due to nitric oxide), ciprofloxacinlactate (effective against *Pseudomonas*), tobramycin (has been used against *Pseudomonas*), ceftazidimpentathydrate (alone or in combination with other antibiotics), gentamicin (is used locally in orthopaedic surgery for the treatment of infections and could be used in local treatment of osteoarthritis), ciproxin, rifampicin (in combination with ceftazidimpentathydrate and/or gentamicin), doxycycline (a broad-spectrum antibiotic) and trimetroprim/sulfamethoxazole (combination).

In some cases, for example when there is concern about side-effects following a systemic treatment, the antibacterial agent will preferably be injected into (or near) the affected osteoarthritic joint. Antibacterial agents in this category include gentamicin and Ciproxin. According to a preferred treatment regimen, 2 or more antibacterial agents will be co-administered e.g. gentamicin and doxycycline. In this case one active agent may be orally administered and the other injected locally.

Particularly preferred embodiment agents are those which are effective against *Janthinobacterium* and/or *Pseudomonas* or *Psuedomonas*-like bacteria.

During the work which led to the present invention, the inventors showed that nitric oxide synthase (which appeared to be bacterial in origin) was differentially expressed in tissues with OA. Nitric oxide synthase has been found to be inhibited even at the transcriptional level by tetracycline compounds and thus such compounds are a preferred class of antibiotics for use in the invention.

The antibacterial agents for use according to the present invention have a sufficiently inhibitory effect on the bacteria within the joint that they cause a measurable and significant improvement in osteoarthritis and its associated symptoms. It is not expected that in all cases treatment will be totally successful but "treatment" according to the present invention should include improvement in one or more of the following areas: pain in and around the joint at rest or on movement, inflammation around the joint, movement of the joint and decay of the cartilage in the joint. Treatment will preferably see an improvement in one or more of these areas but may include prevention or slowing in the further decline of the cartilage, joint movement etc. The nature of OA means that if the development of the disease is arrested, this could be of significant benefit to the patient. If it is intended to introduce engineered tissue or new cells into the site of damage in the joint, then the site is preferably first treated with an antibacterial agent in accordance with the teaching of the invention.

All patients with OA, whether newly diagnosed or at a more advanced stage, can be considered for treatment in accordance with the present invention. Thus, in a further aspect the present invention provides a method of treating a bacterial infection responsible for osteoarthritis in a mammal, which method comprises administering an amount of an antibacterial agent to said mammal which is sufficient to improve one or more of the symptoms of osteoarthritis. Symptoms in which improvement may be observed are discussed above.

Alternatively viewed, according to a method of the invention, a pharmaceutically effective amount of an antibacterial agent is administered to a patient in need thereof in order to treat osteoarthritis.

A 'pharmaceutically effective' amount can be determined with reference to the various areas discussed herein in which treatment may provide measurable improvements, and selected with reference to the Examples.

Generally, patients in need of such a treatment will be diagnosed as suffering from OA by reference to the clinical definitions provided herein or other medically accepted criteria.

Alternatively viewed, the invention provides a method of improving joint mobility and/or reducing pain and/or inflammation of a joint in a mammal which method comprises administering a pharmaceutically effective amount of an antibacterial agent to said mammal.

Likewise, the invention provides the use of an antibacterial agent in the production of a medicament for improving joint mobility and/or reducing pain and/or inflammation of a joint.

An improvement in joint mobility may be assessed by the patient themselves or their medical adviser. Likewise with pain and inflammation.

The present invention also provides a pharmaceutical composition for use in the treatment of OA, more particularly a bacterial infection responsible for OA, said composition comprising an antibacterial agent together with at least one pharmaceutically acceptable carrier, diluent or excipient. The active ingredient in such compositions may comprise from 0.05% to 99% by weight of the formulation, more preferably 0.1% to 5.0%.

By "pharmaceutically acceptable" is meant that the ingredients must be compatible with other ingredients of the composition as well as physiologically acceptable to the recipient.

The pharmaceutical compositions may be formulated according to any of the conventional methods known in the art and widely described in the literature. Thus, the active ingredient may be incorporated, optionally together with other active substances, with one or more conventional carriers, diluents and/or excipients, to produce conventional galenic preparations such as tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions sterile packaged powders, and the like. Other methods of formulating the antibacterial agents, e.g. by incorporation into devices for implantation, are discussed above.

The active agents are preferably formulated into tablets, each tablet containing a predetermined amount of active ingredient. As discussed herein, it may be desirable to inject certain antibiotics into the affected joint.

Suitable doses will vary from patient to patient and can be determined by the physician in accordance with the weight, age and sex of the patient and the severity of the condition and also the particular antibacterial agent selected. A typical total daily dose of antibacterial agent will be in the region of 50-1000 mg, preferably 100-300 mg. This will preferably be administered as a single dose.

Improvements in patients treated in accordance with the present invention may be seen within a week or two and treatment should normally be continued for 1 to 2 months or more to achieve maximum benefits. As shown herein, 4 weeks may be sufficient to see significant improvements.

The identification of a role for bacteria in the development of OA also provides new methods for the accurate diagnosis of OA. Biopsies taken from patients suspected of having OA, e.g. samples of synovial fluid, can be tested for the presence of pathogenic bacteria. Thus, in a further aspect, the present invention provides a method of diagnosing osteoarthritis in a patient, which method comprises testing a sample from a joint of said patient for the presence of (pathogenic) bacteria associated with osteoarthritis. Such a method is preferably in vitro, practised on a sample taken from the patient which is not returned.

A particularly preferred method involves the use of nucleic acid probes or primers designed to detect the bacterial species of interest through homology with a target region (sequence) within the bacteria's nucleic acid. Suitable primers are described herein in the Examples. Preferably the primer or primers target a region within the 16S rRNA (or the gene encoding it). Primers designated herein as F21- and R21-, particularly F21-4 and R21-4 are specific for *Janthinobacterium* type sequences and are especially preferred. The primer pair F21-2 and R21-4 are also particularly suitable.

The probes/primers have homology with target sequences, i.e. they are capable of binding to target sequences under standard levels of stringency.

Methods for obtaining suitable samples from patients suspected of having OA in one or more joints are provided in the Examples herein. The diagnostic method described herein provides a useful and reliable test for confirming that a joint is affected by OA and can be used on its own or together with known diagnostic techniques.

The sample tested will preferably be synovial fluid. If only a little fluid is obtained then saline solution (possibly up to about 30 ml) can be injected before further aspiration. These fluid samples can then be spun down to yield a cell sample, e.g. by centrifuging at 13000-rpm (15000 g) for 45 mins. The cells in the pellet are preferably washed with a sterile saline solution 2-3 times before being frozen, e.g. at −70° C.

The assay for the bacterial gene marker may be based on identification of RNA (e.g. directly for 16S rRNA) or DNA (e.g. the gene encoding 16S rRNA). Where RNA is analysed, a reverse transcription step is required to generate cDNA before PCR can be performed. Methods of analysing RNA are described in the Examples but the DNA from bacteria in the synovial fluid may be analysed instead/as well. The DNA may be first isolated from the cells, e.g. using QIAGEN's DNeasy tissue kit (Cat. No. 69504). Alternatively, the DNA may be amplified and analysed without a separate extraction step. Suitable protocols for amplification of DNA in blood cells is described by Nordvåg, B. et al. in Methods in Neurosciences Vol. 26 [1995] p. 15-25 and in BioTechniques [1992] Vol. 12 No. 4, p. 490-491 and the methods apply equally to a cell sample from synovial fluid.

When performing PCR, preferably three separate primer pairs will be used:

A) a primer set specific for the disease causing bacteria, so specific for *Janthinobacteria* and related species (preferably designed for amplification of the 16S rRNA gene)

B) a primer set for amplification of another gene in the disease causing bacteria which is not as highly conserved as the 16S rRNA genes, e.g. for part of one of the 23S rRNA genes; and C) a human standard gene such as β-actin which can be used for normalization of the amount of bacterial signal to be a signal of human genes derived from human synovial cells.

The assay may quickly and conveniently be performed using only primer set (A) above.

Cells will preferably lyse in a pre-cycle to the PCR method to make the DNA accessible for primer annealing. After PCR, standard gel visualisation techniques are used.

Alternatively viewed, the present invention provides the use of a bacterial detection moiety in the manufacture of an agent for the diagnosis of osteoarthritis. As discussed above suitable bacterial detection moieties include nucleic acid probes and primers which may be designed to detect bacteria generally or a particular genus or species. In particular moieties which can detect the *Janthinobacterium* related species which has been found by the present inventors to be linked to OA. Other moieties for bacterial detection include antibodies.

The 'agent' may simply be a solution, suspension etc. which contains the bacterial detection moiety and is or is capable of being in a form convenient for performing the diagnostic method on a sample. The agent will typically be contacted with the sample in order to determine whether or not bacteria are present.

In a further aspect, the present invention provides a kit for the diagnosis of OA which comprises a bacterial detection moiety, preferably an agent as defined above. The 'bacterial detection moiety' is typically one or more oligonucleotide molecules, e.g. a pair of nucleic acid primers which detect the target bacteria responsible for the OA symptoms. The kit may preferably also include one or more of the following a DNA polymerase (which is as free from contaminating DNA as possible), dNTPs, buffers and a reagent to aid RNA/DNA solubilisation.

In a still further aspect, the present invention provides a product containing (a) an antibacterial agent as defined herein and (b) a nitric oxide antagonist as a combined preparation for simultaneous, separate or sequential use in the treatment of OA, typically the treatment of a bacterial infection which is responsible for OA. A 'nitric oxide antagonist' is any moiety which serves to lower the local nitric oxide concentration in the area surrounding the joint, for example an inhibitor of nitric oxide synthase.

In a further aspect, the present invention provides a product containing (a) an antibacterial agent as defined herein and (b) an agent which can break down DNA, this agent will preferably be an enzyme such as DNaseI, as a combined preparation for simultaneous, separate or sequential use in the treatment of OA, typically the treatment of a bacterial infection which is responsible for OA.

The invention will be further described with reference to the following non-limiting Examples and the Figures in which.

Figure 4:
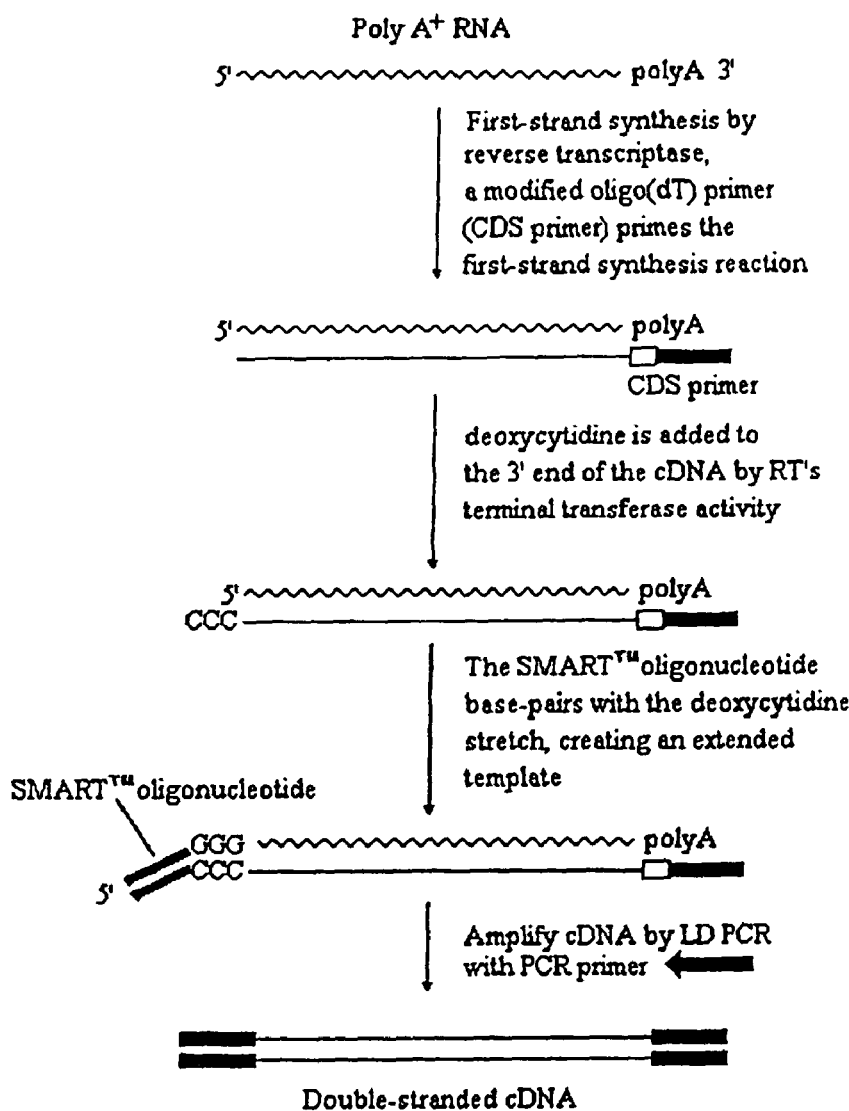

FIG. 4 a flow chart of SMART technology. The figure is adapted from the Clontech SMART™ PCR cDNA Synthesis Kit user manual.

Figure 5:
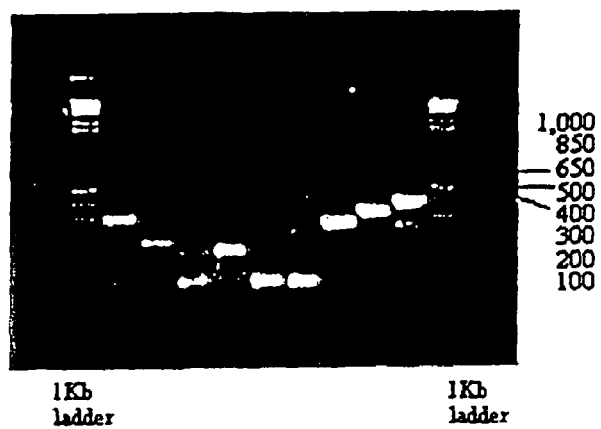

FIG. 5 is a gel photograph showing the results of re-amplification of differentially expressed bands. The bands between 200-600 bp are isolated and used for cloning, sequencing and further verification.

FIG. 6 is the first sequence isolated from patients by differential display. It was a FASTA analysis of this sequence which first lead the inventor to suspect the presence of bacteria.

Figure 7:
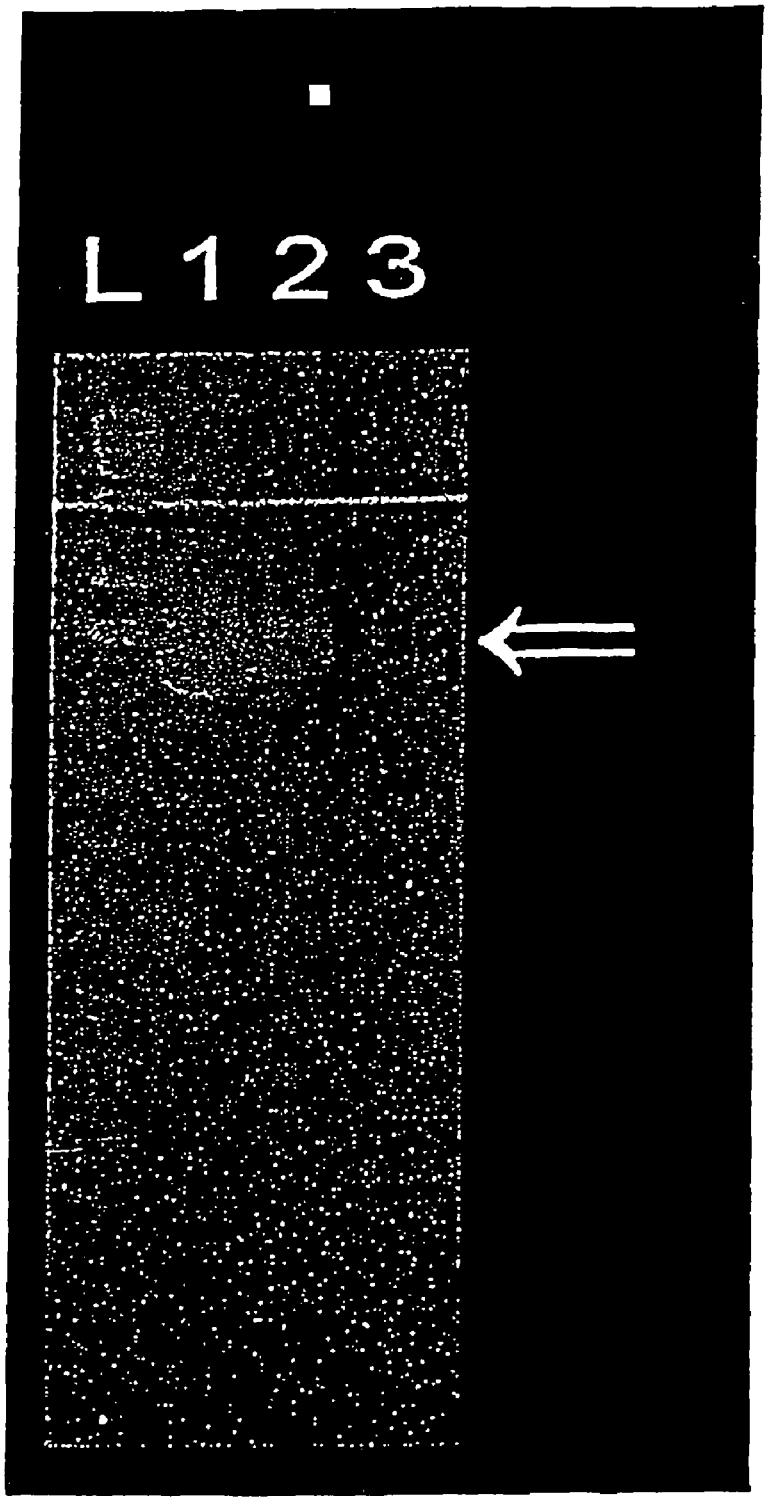

FIG. 7 is a gel photograph showing detection of 16S ribosomal RNA signals from control cultures of *E. coli*. Lane 1=control bacterial RNA, Lane 2=1/10× bacterial RNA, Lane 3=Water. Reverse transcription is performed with primer R1492 and PCR with F27/R1492; 5 µl of each PCR reaction was applied to the gel.

Figure 8:
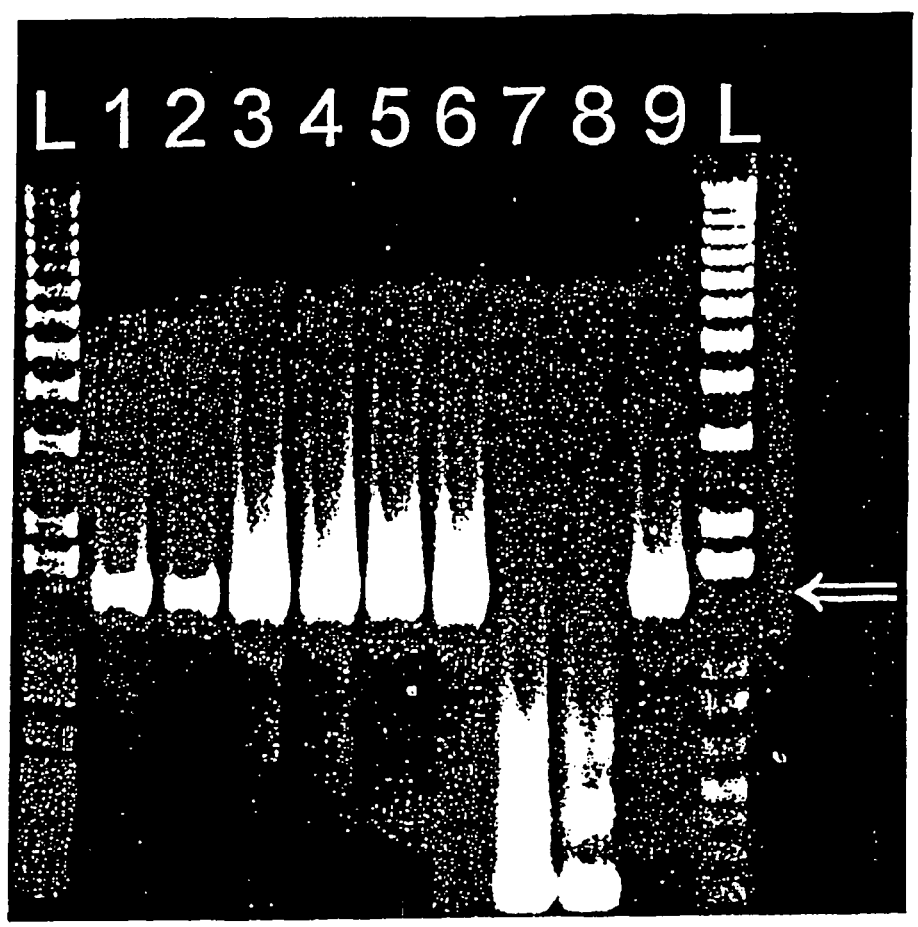

FIG. 8 is a gel photo showing the 16S signal in cartilage biopsies. The lanes were loaded as follows:

| Lane | Sample ID |
|---|---|
| 1 | 8A |
| 2 | 8A |
| 3 | 17A |
| 4 | 17A |
| 5 | 20A |
| 6 | 20A |
| 7 | 16N |
| 8 | 16N |
| 9 | Treated master mix, + primers but no template. |

Reverse transcription was performed with primer R1474, PCR with primers F7/R1474 and 6 µl of each PCR reaction was applied to the gel.

Figure 9:
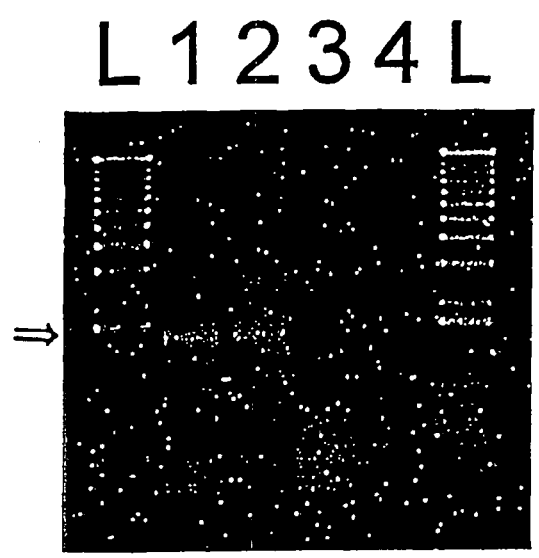

FIG. 9 is a gel photo showing the 16S signal in cartilage biopsies. The lanes were loaded as follows:

| Lane | Sample ID |
|---|---|
| 1 | 8A |
| 2 | 17A |
| 3 | 16N |
| 4 | Water control |

Reverse transcription and PCR were performed using the primers of FIG. 8.

Figure 10:
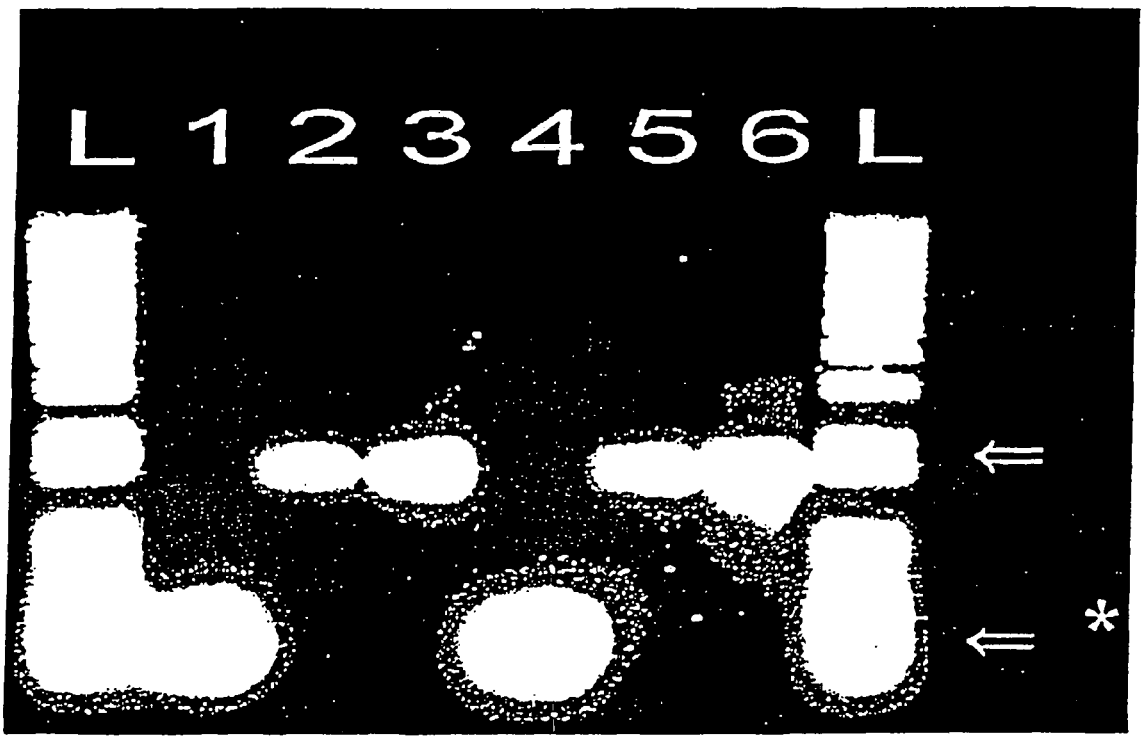

FIG. 10 is a photograph showing purified amplified 16S DNA fragments prior to sequencing. In some samples, especially in normal tissues, a smaller fragment (350 bp) relative to that of the 16S signals (1400 bp), was observed. These smaller fragments when sequenced appeared to be similar to 18S human rRNA. The gel was loaded as follows:

| Lane | Sample ID |
|---|---|
| 1 | 17A small fragment* |
| 2 | 17A large fragment |
| 3 | 20A large fragment |
| 4 | 17A small fragment* |
| 5 | 17A large fragment |
| 6 | Treated master mix, + primers (F7 and R1474) but no template. |

4 µl of each DNA isolate was applied to the gel.

Figure 11:
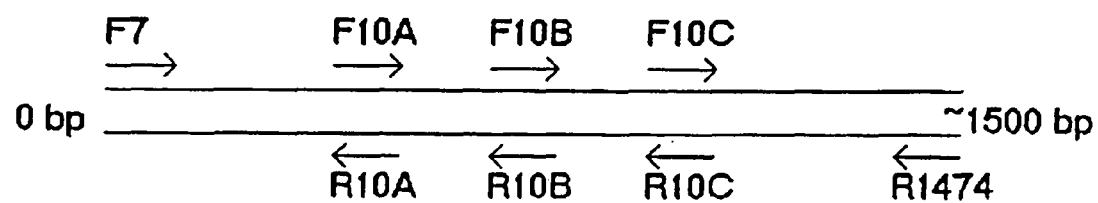

FIG. 11 is a diagrammatic representation showing primer location in full length 16s rRNA. The F7/R1474 pair will amplify the full-length 16s rRNA cDNA but when used for sequencing, these primers will give sequence information for some few hundred base-pairs each, which will not cover the complete sequence. To get the complete sequence of the amplified cDNA, the primers F10A, F10B. F10C, R10A, R10B and R10C are used as additional sequencing primers. The nucleotide sequences are listed in Table 1. In this way, a composite sequence using overlapping sequence information obtained by sequencing with several forward primers is generated. The same process may be done with the reverse primers to obtain a composite reverse sequence and then the forward and reverse sequences compared to make an even more precise composite sequence.

Figure 16:
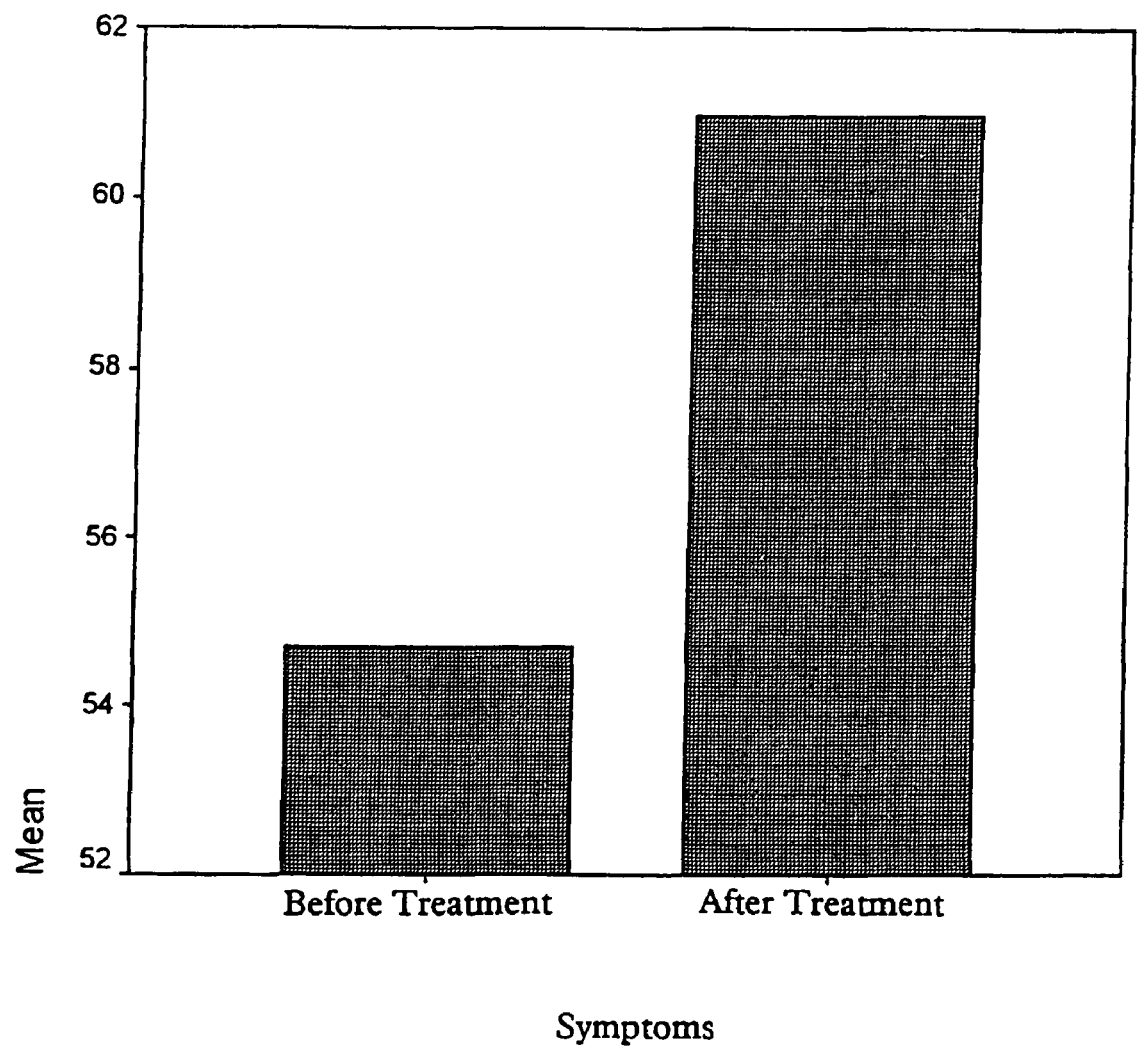

FIG. 12 is the full length 16s RNA sequence obtained as a forward and reverse composite sequence from patient number 21, A region, using the primers described in the legend to FIG. 16. This sequence was always found in osteoarthritic patents and was found by a Blastn search of the NCBI database to represent *Janthinobacterium*.

FIG. 13 is a schematic representation of how different primers may be used to differentiate between *Janthinobacterium* (J) and *Burkholderia* (B) 16s rRNA sequences. These sequences are generally rather similar but with regions where there is a high percentage of mismatch between the two species. Thus, F25-/R25-primers will amplify templates with a B-type sequence and F21-/R21-primers will amplify templates with a J-type sequence. This technique helped in reaching the conclusion that the bacterial species involved in OA was *Janthinobacterium* or very closely related thereto and in identifying the best primers for use in diagnosis of OA caused by bacterial infection, F21-1 and R21-4.

Figure 14:
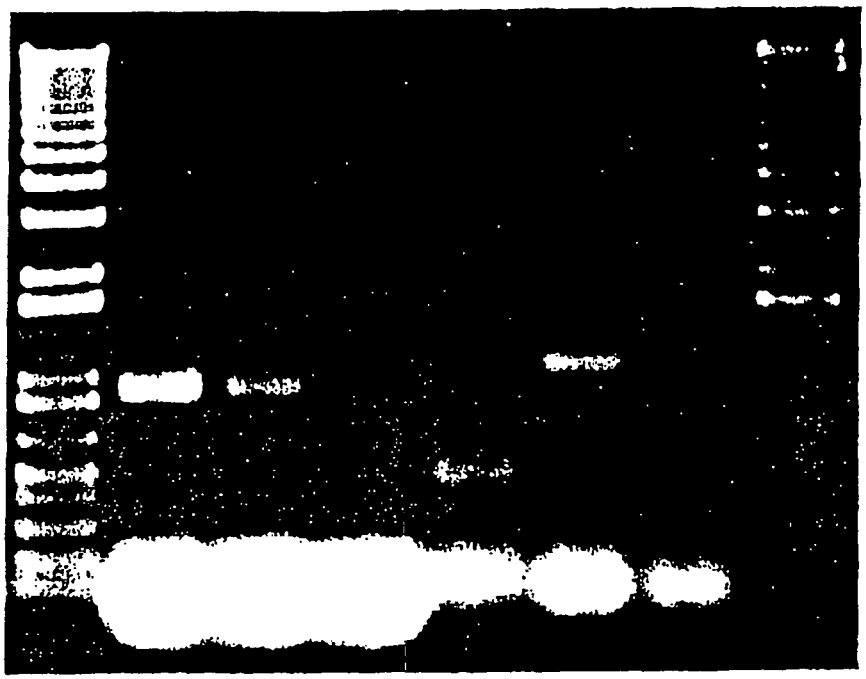

FIG. 14 is a gel photograph showing detection of pathogen 16s rRNA genes in synovial fluid. DNA was isolated from synovial fluid from an arthritic knee using the TRIzol kit from Gibco BRL/Life Technologies. The 16s rRNA sequence was amplified using primers designed from the 16s rRNA sequence found in sample 21A. The gel was loaded as follows:

| Lane | Sample | Primers |
|---|---|---|
| 1 | DNA | F21-1/R21-4 |
| 2 | DNA ¹⁄₁₀ dilution | F21-1/R21-4 |
| 3 | Water control | F21-1/R21-4 |
| 4 | DNA | F21-1/R21-5 |
| 5 | DNA ¹⁄₁₀ dilution | F21-1/R21-5 |
| 6 | Water control | F21-1/R21-5 |
| L | 1 kb Plus DNA ladder, Gibco BRL/Life Techologies | |

Figure 15:

FIG. 15 is a gel photograph showing a failure to detect bacterial 16S rRNA in samples from patient 31, normal (N) region and in a water control. The lanes were loaded as follows:

| Lane # | Sample | Forw. Prim. | Rev. Prim. |
|---|---|---|---|
| L | 1 kb+ ladder | | |
| 1 | 31N-SF DNA ¹⁄₁₀ dil. | F25-1 | R25-3 |
| 2 | 31N-SF DNA ¹⁄₁₀ dil. | F25-1 | R25-4 |
| 3 | 31N-SF DNA ¹⁄₁₀ dil. | F25-1 | R25-5 |
| 4 | 31N-SF DNA ¹⁄₁₀ dil. | F25-2 | R25-3 |
| 5 | 31N-SF DNA ¹⁄₁₀ dil. | F25-2 | R25-4 |
| 6 | 31N-SF DNA ¹⁄₁₀ dil. | F25-2 | R25-5 |
| 7 | 31N-SF DNA ¹⁄₁₀ dil. | F25-3 | R25-4 |
| 8 | 31N-SF DNA ¹⁄₁₀ dil. | F25-3 | R25-5 |
| 9 | Water Ctrl. | F25-1 | R25-3 |
| 10 | Water Ctrl. | F25-1 | R25-4 |
| 11 | Water Ctrl. | F25-1 | R25-5 |
| 12 | Water Ctrl. | F25-2 | R25-3 |
| 13 | Water Ctrl. | F25-2 | R25-4 |
| 14 | Water Ctrl. | F25-2 | R25-5 |
| 15 | Water Ctrl. | F25-3 | R25-4 |
| 16 | Water Ctrl. | F25-3 | R25-5 |

If bacteria had been present in any of the samples (even species other than *Burkholderia*) then a signal should have been generated using these forward and reverse primers.

FIG. 16 is a graph showing the KOOS scores for 'symptoms' before and after treatment with an antibiotic. p=0.100

Figure 17:
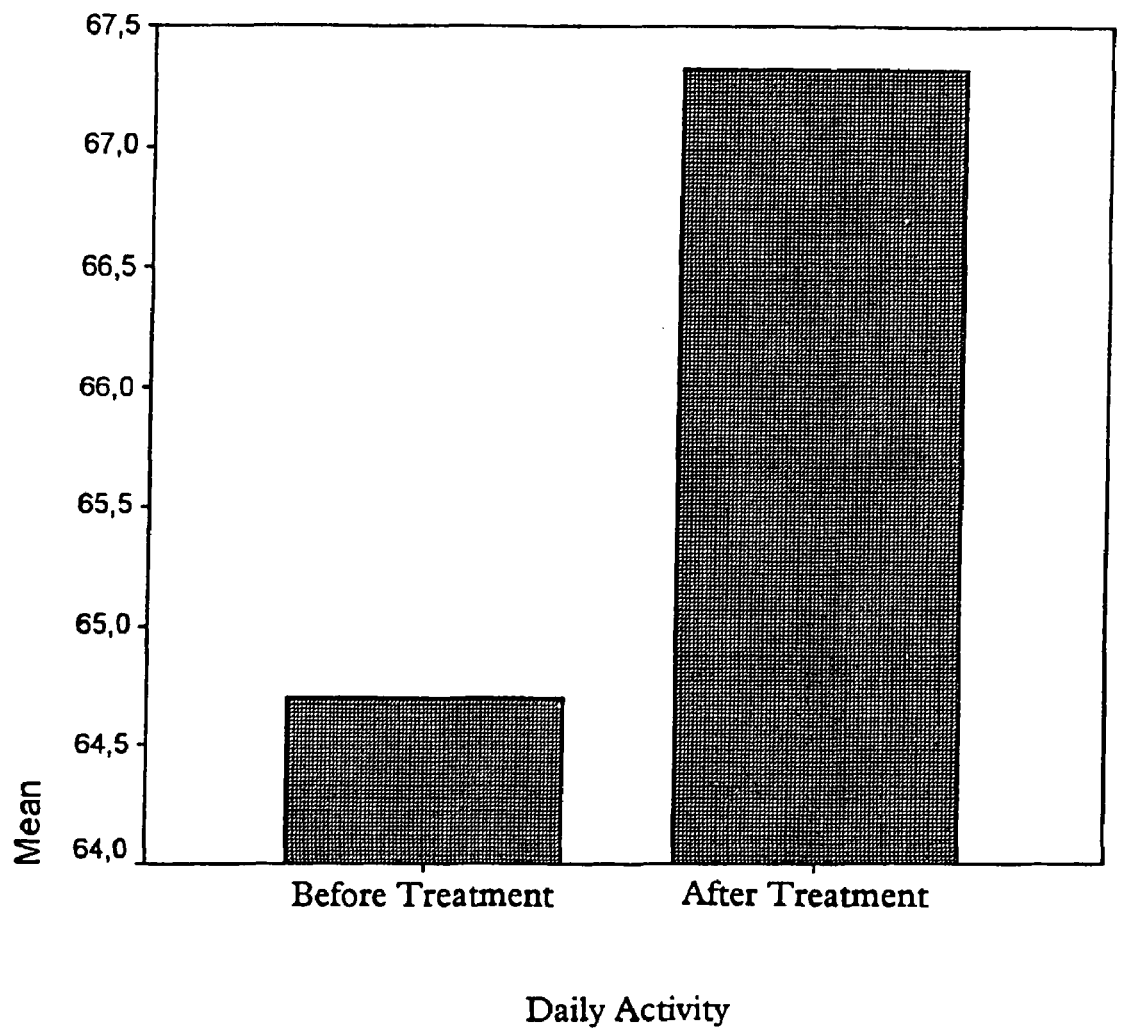

FIG. 17 is a graph showing the KOOS scores for 'daily activity' before and after treatment with an antibiotic. p=0.429.

Figure 18:
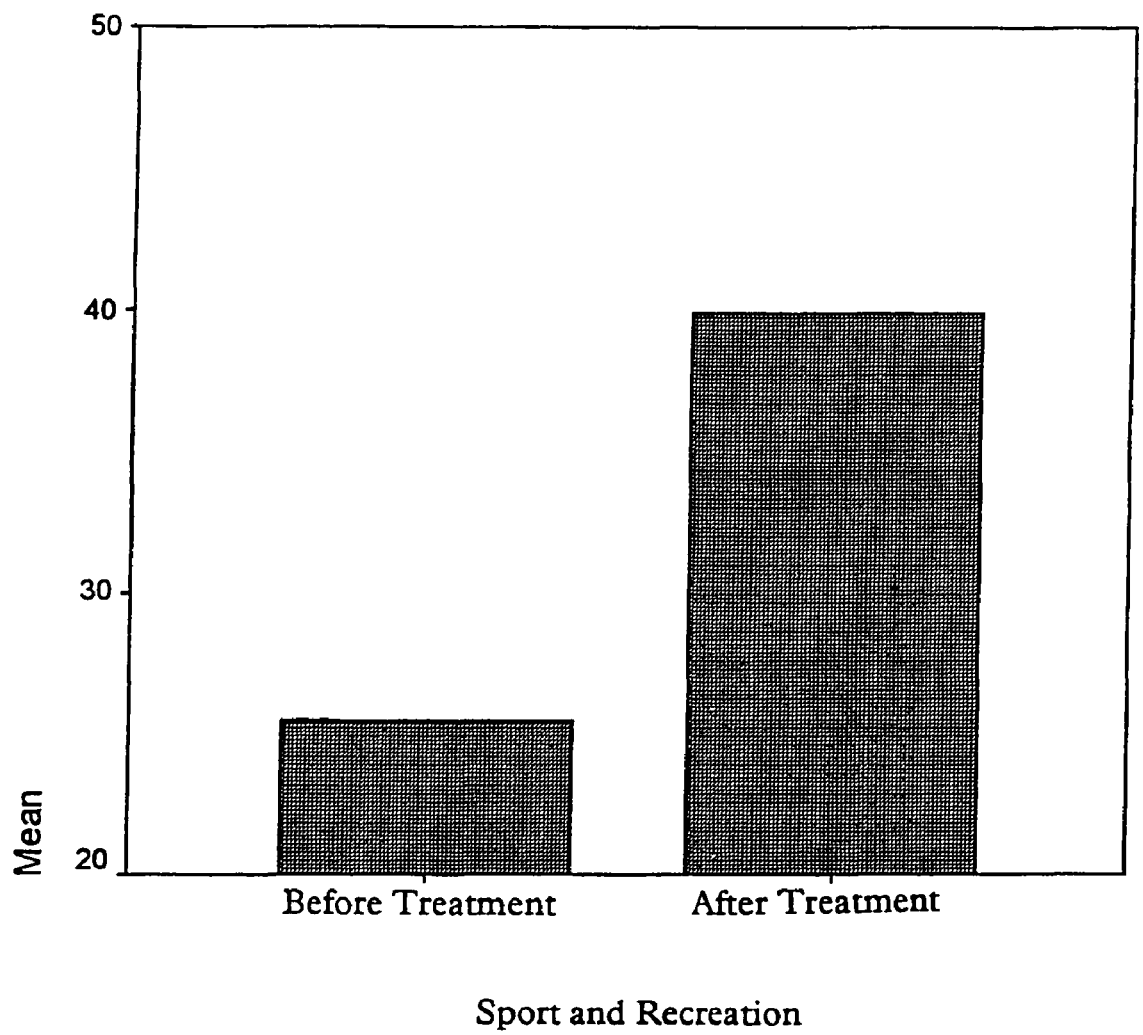

FIG. 18 is a graph showing the KOOS scores for 'Sport and Recreation' before and after treatment with an antibiotic. p=0.008.

Figure 19:
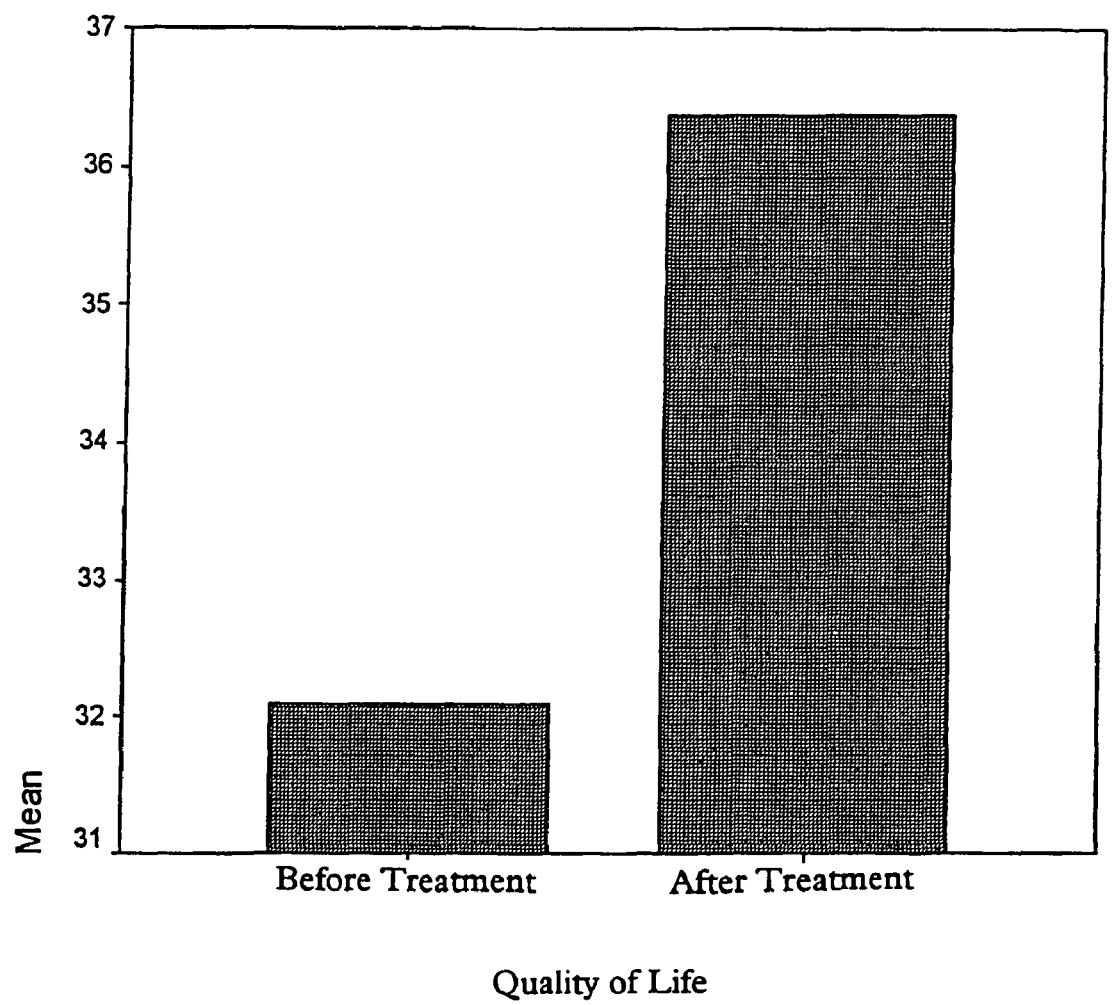

FIG. 19 is a graph showing the KOOS scores for 'Quality of Life' before and after treatment with an antibiotic. p=0.182.

Figure 20:
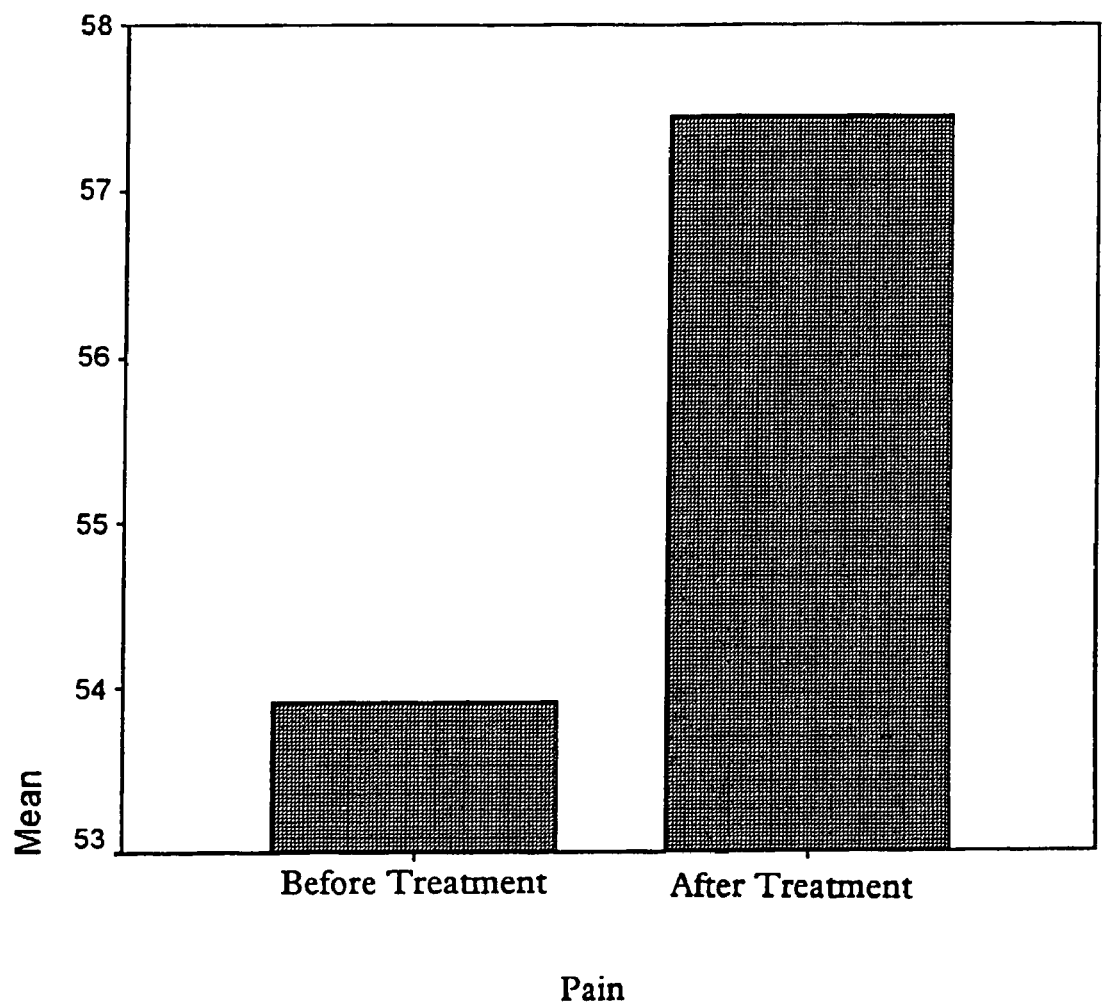

FIG. 20 is a graph showing the KOOS scores for 'Pain' before and after treatment with an antibiotic. p=0.386.

Figure 21:
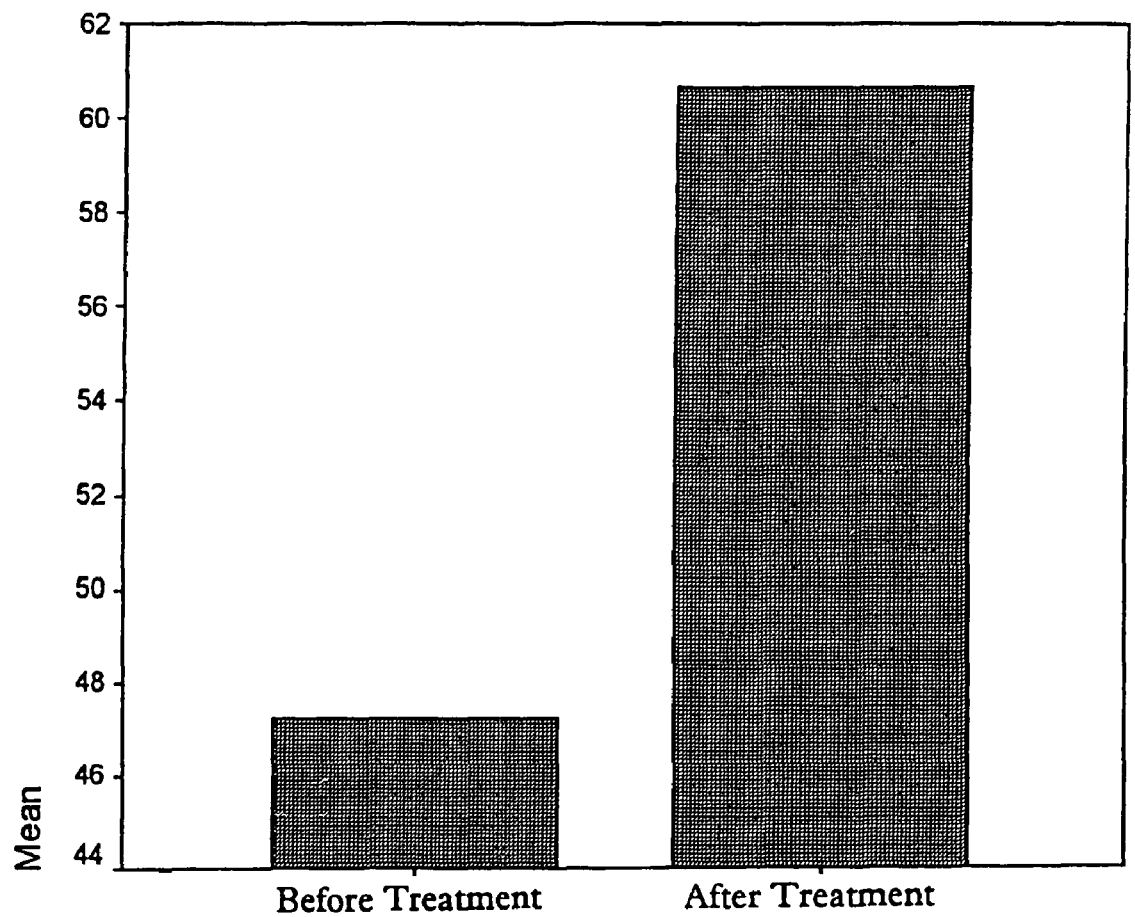

FIG. 21 is a graph showing the Lysholm single scores before and after treatment with an antibiotic. p=0.003.

EXAMPLES

Example 1

Identification of Bacteria Associated with Osteoarthritic Damage

Clinical Cartilage Biopsies

The ethical committee at Tromsø University Hospital approved the removal and examination of cartilage for this study. Patients undergoing the biopsy procedure, were informed orally and written about the project, and signed a document telling that they accepted the use of the material for this research project.

Figure 1:
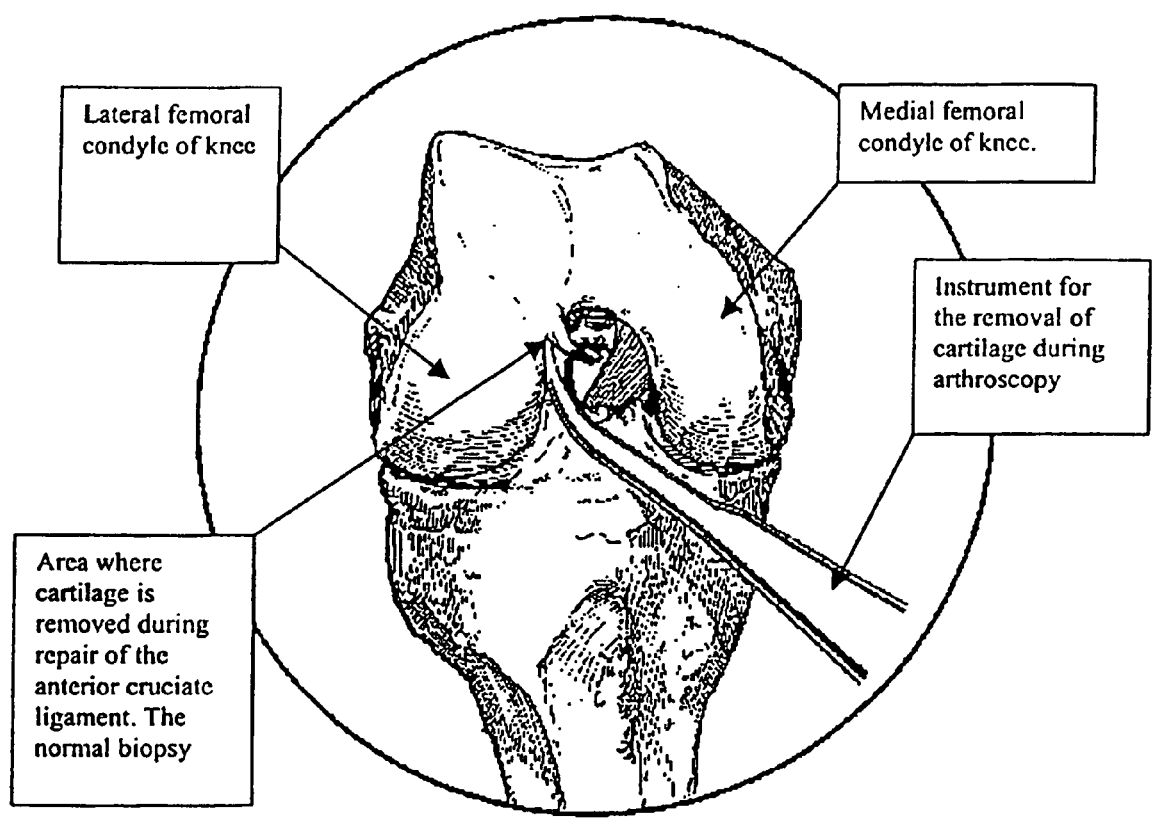
FIG. 1 is a sketch showing notchplasty during reconstruction of the anterior cruciate ligament. Cartilage is removed from the lateral wall of the notch.

The three different qualities of cartilage tissues, normal, focally damaged and osteoarthritic, were taken from patients in the following way:

1. The normal cartilage (N) was taken from knees undergoing anterior cruciate ligament reconstruction. To repair the ligament, a graft including a piece of bone from patella, a part of the patellar ligament, and an amount of bone from the proximal tibia were used. When placing the graft into the knee, the procedure includes the removal of some cartilage from the lateral femoral condyle of the knee (FIG. 1). This is done to allow sufficient space for the new ligament in flexion and extension of the knee. None of the knees which were used for harvesting normal cartilage had a history of trauma for the last two months, and there were no signs of actual inflammation in these knees. The removed cartilage was used as the normal tissue sample. During operation it was taken out under sterile conditions, and immediately immersed frozen in liquid nitrogen. Samples were later stored at −75 C.

Figure 2:
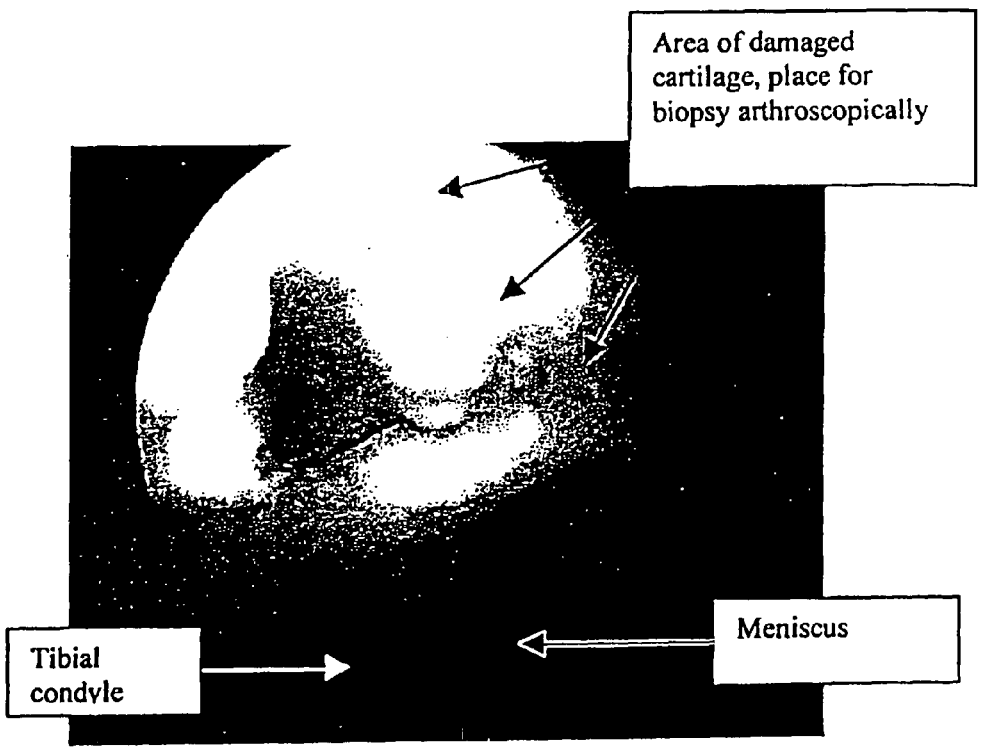
FIG. 2 is a photograph based on optical visualisation showing focally damaged cartilage on the medial femoral condyle. The picture was taken during arthroscopy.

2. The focally damaged cartilage (D) was from areas in knees removed during repair with chondrocyte transplantation (FIG. 2), a technique described by Mats Brittberg and coworkers in 1994 (Brittberg M., Landahl A., Nilsson A., Ohlsson C., Isaksson O., Peterson L., N. Engl. J. Med. 1994, Oct. 6; 331(14): 889-95). This technique includes taking a biopsy from the knee which is to be repaired from a not weight bearing area of the knee, and from this biopsy the cells are isolated and allowed to multiply in vitro for about three weeks. When a sufficient number of cells is reached, the cells are transplanted into the knee after removal of the damaged cartilage area. The removed and damaged cartilage was used as a sample of damaged cartilage. Also this biopsy was removed under sterile conditions.

Figure 3:
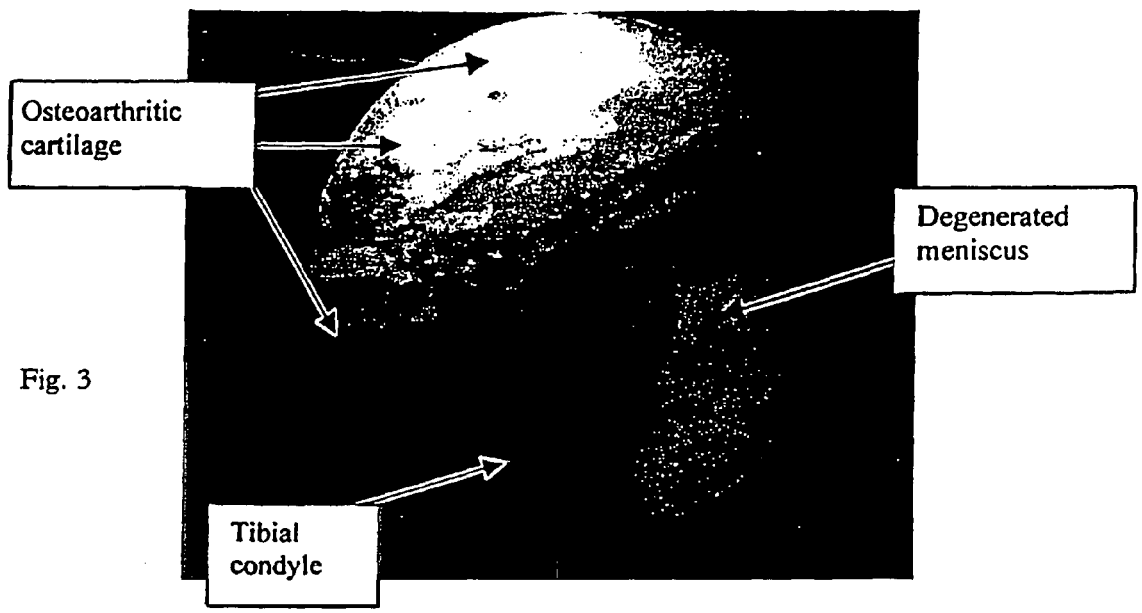
FIG. 3 is a photograph based on optical visualisation showing advanced osteoarthritic changes in a knee, again the picture was taken during arthroscopy.

3. The osteoarthritic cartilage (A) (FIG. 3) was removed during operation from patients with advanced osteoarthritis to a degree excluding the cell transplantation technique. These knees underwent joint replacement surgery, using prosthesis. During the operative procedure, the cartilage has to be removed, and areas of cartilage with the most advanced changes were taken, harvested under sterile conditions.

Details of Other Materials Used in the Experiments

Primers

The following primers were used. R (reverse) primers R-1492 and R-1474 were used for reverse transcription. For PCR, generally the F-27/R-1492 and the F-7/R-1474 pairs were used (F=forward). The sequence of the primers is indicated in Table 1 below.

The primers were bought from Sigma-Genosys. For cDNA synthesis the primers were diluted to 2.5 pmol/µl in water. For PCR the primers were diluted to 50 pmol/µl in water.

F-7/R-1474 are preferred for identification of bacterial 16S rRNA (or the gene encoding it) generally as they anneal to a sequence conserved among several studied bacterial species. F21-2/R21-4 are suitable for identification of the key causal bacterium *Janthinobacterium* (or closely related species).

TABLE 1

| Primer | Primer Sequence |
|---|---|
| F2521 | 5'-GCA AGT CGA ACG GCA GCA CGG GT-3' |
| F25-1 | 5'-GGA TAG CCC GGC GAA AGC CGG AT-3' |
| F25-2 | 5'-CCT TCG GGC CTC GCG CTA TAG GGT T-3' |

TABLE 1-continued

| Primer | Primer Sequence |
|---|---|
| F25-3 | 5'-TCC TTG GCC CTA ATA CGG TCG GGG G-3' |
| R25-3 | 5'-CCC CCG ACC GTA TTA GGG CCA AGG A-3' |
| R25-4 | 5'-TCC ACC TCT CAG CGG AAT TCC GA-3' |
| R25-5 | 5'-GCA ACC CTC TGT TCC GAC CAT TGT-3' |
| R2521 | 5'-GAT TAG CTC CCC CTC GCG GGT TGG-3' |
| F21-1 | 5'-GGG ATA ACG TAG CGA AAG TTA CGC TA-3' |
| F21-2 | 5'-TCG CAA GAC CTC ATG CTC GTG GAG C-3' |
| F21-3 | 5'-CGG TGA GAG CTA ATA TCT CTT GCT AAT-3' |
| R21-3 | 5'-ATT AGC AAG AGA TAT TAG CTC TCA CCG-3' |
| R21-4 | 5'-CCC TGA TCT CTC AAG GAT TCC AGC C-3' |
| R21-5 | 5'-GCG GCG CTC TGT ATG TAC CAT TGT ATC-3' |
| F-7 | 5'-ATC CTG GCT CAG ATT GAA CG-3' |
| R-1474 | 5'-TCA CCC CAG TCA TGA ATC CT-3' |
| F-27 | 5'-AGA GTT TGA TC(C/A) TGG CTC AG-3' |
| R-1492 | 5'-TAC GG(C/T) TAC CTT GTT ACG ACT T-3' |
| F10A | 5'-GTG AGT GAA GAA GGC CTT CG-3' |
| F10B | 5'-TGG GGG ATT CAT TTC CTT AG-3' |
| F10C | 5'-AGC AGC CGC GGT AAT ACG-3' |
| R10A | 5'-ATG ACG TGT GAA GCC CTA CC-3' |
| R10B | 5'-TTA ATC CAC ATC ATC CAC CG-3' |
| R10C | 5'-AGC CCG GGG ATT TCA CAT-3' |
| F27' | 5'-AGA GTT TGA TC(C/A) TGG GTC AG-3' |
| F-8 | 5'-AGA GTT TGA TCC TGG YTC AG-3' |
| R-556 | 5'-CTT TAC GCC CAR TAA WTC CG-3' | cDNA Synthesis

The Superscript II RNase H⁻ Reverse Transcriptase (Cat. No. 18064-014) from GibcoBRL/Life Technologies were used with its buffer and DTT. dNTP's (Cat. No. U1240) were purchased from Promega.

Agarose Gel Electrophoresis and DNA Isolation

SeaKem LE Agarose (Cat. No. 50004) from MedProbe were used for gel electrophoresis.

QIAEX II Gel Extraction Kit (Cat. No. 20021) from QIAGEN were used for DNA isolation from agarose.

Sequencing Kit and Conditions

Thermo Sequenase Cy-5 Dye Terminator Kit (Cat. No. 27-2682-01) from Amersham Pharmacia Biotech were used for the sequencing reactions. Sephadex G-50 (Cat. No. 9048-71-9) from Sigma were used for the Sequencing PCR product purification. The ABI PRISM BigDye Terminator Cycle Sequencing Kit could also be used.

PCR Reagents

HotStarTaq DNA polymerase (Cat. No. 203205) from Qiagen were used for PCR amplification of 16S ribosomal RNA.

PCR master mixes were treated with RQ1 RNase free DNase I (Cat. No. M610A) from Promega.

Water

RNase free, DNase free, DEPC treated, autoclaved, 0.2 µM filtered water (Cat. No. 9915G) from Ambion were used when preparing RNA, synthesizing cDNA and during PCR.

Differential Display Method

The following technique combines amplification of complete length cDNA with differential display.

SMART cDNA PCR (Clontech Laboratories Inc., PR304-1) is a technique originally developed to amplify complete cDNA populations/libraries. First strand cDNA is synthesized utilizing a oligo-dT primer (CDS primer). The reverse transcriptase (MMLV, RNase H—) adds a small number of cytidine residues after completing the first strand. A second primer (SMART II primer) anneals to the dC-"tail" and the reverse transcriptase switches template. The primers are designed to give the same sequence at both ends of the cDNA and thus by using a primer that will bind to both ends (PCR primer) we can amplify the total mRNA (as cDNA) population exponentially.

We have used SMART cDNA PCR to amplify cDNA constructed from very small mRNA samples. We have then used the amplified cDNA as template in differential display reactions.

Materials and Methods

Sample material were taken from a patient being operated for unicompartment arthrosis in his knee, see Example 1. Biopsies were taken from the osteoarthritic part of the cartilage. From the same knee normal cartilage was taken from the undisturbed area. The cartilage samples were frozen in liquid Nitrogen within 5 minutes and then stored at −75° C. until RNA extraction was performed.

RNA Extraction

The cartilage were homogenized to a fine powder with a mortar and pestle in liquid Nitrogen. Total RNA was isolated using TRIZOL reagent from Gibco (#15596). RNA concentration and quality were determined by measuring Abs 260/280 and by running a sample on an agarose gel.

cDNA Synthesis

Reverse Transcriptions were done using the SMART PCR cDNA Synthesis Kit from Clontech (#K1052-1). The manufacturer's recommended conditions were followed. 3 µl of RNA solution were used. MMLV reverse transcriptase (200 U/µl)(Gibco 18064-014) were used.

cDNA Amplification

Total cDNA was amplified using the SMART PCR cDNA Synthesis Kit (# K1052-1) from Clontech. The manufacturer's recommended conditions were used. 2 µl first-strand cDNA were amplified in a total volume of 50 µl with Advantage 2 KlenTaq Polymerase from Clontech (#8430-1). After 25 cycles the PCR product were examined on an agarose gel and DNA concentration were determined by measuring Abs 260/280.

Differential Display; Using Two Primers:

For the Differential Display reactions the Delta Differential Display Kit (#K1810-1) from Clontech was used. The manufacturer's recommended conditions were used. The amplified cDNA was diluted to 0.02 µg/µl. Several primer combinations (T and P primers included in the kit) were used to screen for differentially expressed genes.

1 µl of the cDNA dilutions was used as template in each reaction. The samples were labelled with [α]-$^{33}$P dATP (Amersham) and amplified with Advantage 2 KlenTaq Polymerase (#8417-1) from Clontech. Following three low-stringency cycles 25 high-stringency cycles were run. The PCR products were separated on a sequencing gel (7 M Urea, 4% acrylamide (37, 5:1) 0.5×TBE) with 0.2 mm spacers at 500V until the bromophenol blue dye had left the gel. The gels were visualized by exposing them to BioMax MR film for ½-1 days.

Differentially expressed bands were excised from the dried gels by superimposing the film to mark the bands prior to isolate the gel material using a scalpel. 100 µl water was added to each gel slice in an eppendorf tube. The slices were then incubated at 37° C. overnight. The tubes were spun down at 14000 g for 15 minutes at 4° C. The eluate were then stored at −20° C. 5 µl of each eluate was used as template in an amplification reaction using the same conditions as in the Differential Display PCR (no labelling). The PCR products were examined on an agarose gel. Some smear was evident and a larger volume was separated on a larger gel. The bands of interest were cut from the agarose gel and the DNA was isolated using the QIAEX II Kit from Qiagen (#20021). The manufacturer's procedure was followed. DNA was eluted in 20 µl of water. The DNA was reamplified again using pfu Turbo polymerase (#600252-51). Each 50l reaction contained 1 µl template, 40 PM primer T and P, 100 µM dNTP, 10× buffer and 1.25 U of enzyme. PCR was run with the following conditions: Initial 94° C. 9 min, 43 cycles of 94° C. for 30 sec and 60° C. for 1 min and a final elongation at 60° C. for 10 min.

After examining a test run on an agarose gel parallel reactions on 2 tubes were run and the products pooled. The DNA was isolated from the PCR reaction mix using the QIAEX II DNA Purification System from Qiagen. The manufacturer recommendations were followed. The DNA was eluted in 15 µl of water. A sample was run on an agarose gel. Upon visualization there were no additional bands or smear visible.

Cloning

The reamplified cDNA was cloned into pGEM-T easy cloning vector (#A1360, Promega, Madison, Wis., USA). The ligation was performed with a vector concentration of 50 ng/µl. The presence of a plasmid insert of the expected size was assayed by PCR using the same primers as in the differential display and by cutting the vector with the restriction enzyme EcoRI.

The cloned PCR fragments were sequenced using the T7 primer. The sequences found showed strong homology with known human gene sequences. They were also 3-4 times longer than the average EST.

Differential Display Using One Primer:

Random 10-mer primers (Operon Technologies, Alameda, Calif., USA) were used to amplify cDNA with no radioactivity. Each 50 µl reaction contained 1 µl of cDNA, 80 µM of one primer, 200 µM of each dNTP, 10× buffer and 2.5 U of HotStarTaq polymerase (Qiagen). PCR was run with the following conditions: Initial 95° C. 15 min, 40 cycles of 94° C. for 2 min, 38° C. for 2 min and 68° C. for 1 min and 25 sec, and a final elongation at 72° C. for 10 min. The PCR amplification products were separated on a 1.5% agarose gel (agarose 1000, Gibco) in TAE buffer with 1 mM guanosine, and visualized with ethidium bromide. Agarose 1000 is able to resolve bands separated by 10 bp. Differentially expressed bands were excised, isolated and cloned into pGEM-T easy vector without additionally amplification.

Results

One important aspect of our strategy is to amplify the total cDNA population prior to using it as template in Differential Display PCR reactions using Clontech Smart™ PCR Kit (FIG. 4).

Comparison of Differential Display PCR products from cartilage samples (healthy and osteoarthritic) showed genes expressed in one sample but not in the other.

After Differential Display the cDNA can be eluted from the gel material. The cDNA can then be reamplified using the same primers (RT PCR) as in the Differential Display procedure (FIG. 5).

Gene Rescue from the Library by Reverse PCR

After sequencing, two internal primers with 100% overlap were designed. These internal primers were used to amplify the whole gene using cDNA library in pTriplEx2 vector (Clontech) as template. The cDNA was packaged in λ TriplEx2 which is converted to pTriplEx2 by transduction into *E. coli* BM25.8. Using the pTriplEx2 cDNA library with the decided internal primers, only the plasmid with the gene of interest is amplified. The primers are designed from the sequence of a differentially expressed gene. After transformation into JM109, the differentially expressed gene is sequenced.

Identification of Bacterial 16S Ribosomal RNA in Cartilage Samples

RNA Extraction

The fresh-frozen cartilage tissues were homogenized to a fine powder with a mortar and pestle on liquid Nitrogen. Total RNA was isolated using TRIZOL reagent from Gibco (#15596). RNA quality was determined by running a sample on an agarose gel electrophoresis.

First Strand cDNA Synthesis

The following were mixed in an eppendorf tube:

| | |
|---|---|
| 2 µl | RT primer (R1474, 5 pmol) |
| 2 µl | RNA sample |
| 8 µl | H₂O (DEPC treated, RNase-free) |

The tube was heated to 90° C. for 5 min, then cooled slowly at room temperature.

RT-PCR Master-Mix were prepared:

| | /One reaction |
|---|---|
| 4 µl | 1St Strand buffer |
| 2 µl | 0.1M DTT |
| 1 µl | 10 mM dNTP's |

To each reaction 7 µl RT-MasterMix were added and the tube was then incubated at 42° C. for 2 min.

To each reaction 1 µl Superscript II Reverse Transcriptase was added. The tubes were then incubated at 42° C. for 50 min. The reactions were stopped by heating at 100° C. for 10 min. The tubes were then quickly placed on ice.

80 µl of DEPC treated water were then added to each tube.

PCR Amplification

Preparation and DNase treatment of PCR-MasterMix

| 1 × rxn | |
|---|---|
| 5 µl | 10× buffer |
| 2 µl | 25 mM Mg²⁺ |
| 1 µl | 10 mM dNTP's |
| 37.5 µl | H₂O |
| 2.5 µl | DNase I |

The PCR-MasterMix were incubated at 37° C. for 1 hour, then boiled for 5 minutes and placed on ice. The following reagents were added.

| | 1 rxn | |
|---|---|---|
| 1 µl | PrimerMix (50 pm/µl of forward primer + 50 pm/µl of reverse primer | |
| 0.25 µl | HotStarTaq DNA polymerase | |

For each PCR reaction 1 µl 1'st strand cDNA were mixed with 49 µl of PCR-MasterMix in a 0.2 ml PCR-tube.

The following PCR were run on a MJ Research PTC-200 Peltier Thermal Cycler.

| 95° C. | 8 min |
|---|---|
| 12× | |
| 95° C. | 40 s |
| 70° C. | 40 s |
| | −1° C./cycle |
| 72° C. | 2 min |
| 15× | |
| 95° C. | 40 s |
| 58° C. | 40 s |
| 72° C. | 2 min |
| 20× | |
| 95° C. | 40 s |
| 56° C. | 40 s |
| 72° C. | 2 min |
| 4° C. | hold |

The PCR products were then stored at −20° C.

Agarose Gel Electrophoresis

The PCR products were run side-by-side on an 0.8% agarose gel. Mini gels (6×10 cm) were run for 50 min at 90 V in 1×TAE buffer. For Mini gels a typical sample was 6 µl PCR product. A 1 kb Plus DNA ladder from Gibco were run parallel to the samples for DNA fragment size determination.

The gels were stained in EtBr solution (0.5 µg/ml water) for 20 minutes. They were then destained in several washes of water for about 40 min.

The gels were visualized on a BioRad Gel Documentation system.

DNA Isolation from Agarose Gel

Four identical PCR reactions were run in parallel, for the preparative isolation of DNA for sequencing. The combined products were then run on a gel with large wells. The same conditions as in the previous visualization were used. After staining the gels were laid on a low intensity UV transilluminator and the bands of interest were quickly excised with sterile scalpels. We have found out that soaking the gel in 1 mM guanosine solution (Grundemann and Schomig) prior to UV visualization of the bands eliminated the complications in DNA sequence due the UV damage of the DNA. A typical gel piece weighed about 150-200 mg.

DNA was isolated from the gel fragments using the QIAGEN QIAEX II Gel Extraction Kit (Cat. No. 20021). The manufacturers conditions were followed. The DNA fragments were eluted in 25 µl 10 mM Tris-HCl, pH 8.5.

The quality of the isolated DNA was checked by running a small amount (2 µl) on a Mini gel as described before. An example of purified DNA fragments isolated prior to DNA sequencing is shown in FIG. 10.

DNA Sequencing

Cy-5 dNTP Mixes

For four sequencing reactions four Cy-5 dNTP mixes were made (A,C,G,T).

| 4 rxns (MA, MC, MG, MT mixes) | |
|---|---|
| 2 µl | 1.1 mM dNTP's |
| 1 µl | Cy-5 dNTP (A, C, G or T) |
| 7 µl | H$_2$O |
| 1 µl | 0.55 mM EDTA |

Tubes containing Cy-5 dNTP's must at all times be kept on ice in the dark.

A sequencing master mix were made.

| | 1 rxn |
|---|---|
| 8 µl | DNA template |
| 2 µl | primer (forward or reverse) |
| 3.5 µl | rxn buffer |
| 0.9 µl | Thermo Sequenase |
| 12.6 µl | H$_2$O |

In four PCR tubes the following were added.

| A: | 2 µl | MA |
|---|---|---|
| C: | 2 µl | MC |
| G: | 2 µl | MG |
| T: | 2 µl | MT |

To each of the four tubes 6 µl of sequencing master mix were added.

The following PCR were run:

| 30× | |
|---|---|
| 95° C. | 30 s |
| 57° C. | 30 s |
| 72° C. | 80 s |

The sequencing reaction products were purified on Sephadex G-50 spin columns (96 well array). The products were then dried in the dark at 37° C. and then resuspended in sequencing stop solution (8 µl). The samples (4 µl) were then run on an Amersham-Pharmacia ALF sequencer under standard conditions.

Results

Detection of 16 S RNA in Cartilage from Patients with Osteoarthritis

PCR Results

After we have managed to test the protocol by detecting 16S RNA using diluted bacterial cultures of *Escherichia coli* (FIG. 7) we tested this method on cartilage clinical samples.

Designation of lanes/tissues are (N) for normal or non-affected regions, (D) for Damaged and (A) for osteoarthritic. A joint from one patient may have regions of obviously advanced OA, regions which look quite normal and areas which are not in the advanced stages of OA but where the cartilage is soft and to a certain degree fibrillated, this last area is defined as damaged.

The results are shown in the Figures and Table 2 below. The results show that the presence of 16S signals can always be associated with osteoarthritic patients. Although occasionally tissue isolated from osteoarthritic patients did not reveal 16S RNA signals using the standard PCR conditions, no 16S RNA signal was ever detected in tissues from normal patients.

Table 2 below gives a summary of the detection of 16s rRNA sequences in clinical samples. A=Osteoarthritic and N=normal. Two types of control were used, H$_2$O control (blank) and *E. coli* total RNA as a positive control. Reverse transcription is done with primer R1474. PCR amplification was performed using F7 and R1474 primers. The numbers in the 'sample' column are the patient numbers. Some samples appear more than once in the table because the sample was analysed on more than one day.

TABLE 2

| Sample | Positive | Negative |
|---|---|---|
| 8A | * | |
| 17A | * | |
| 20A | * | |
| 16N | | * |
| *E. coli* ctrl | * | |
| H$_2$O | | * |
| 8A | * | |
| 17A | * | |
| H$_2$O | | * |
| 8A | * | |
| 17A | * | |
| 16N | | * |
| H$_2$O | | * |
| 8A | | * |
| 17A | * | |
| H$_2$O | * | |
| 21A | * | |
| H$_2$O | | * |
| 21A | * | |
| H$_2$O | | * |
| 25A | * | |
| H$_2$O | | * |
| 25A | * | |
| H$_2$O | | * |
| 25A | * | |
| H$_2$O | * | |
| 25A | * | |
| H$_2$O | | * |
| 25A | * | |
| H$_2$O | | * |
| 25A | * | |
| 21A | * | |
| H$_2$O | * | |

TABLE 2-continued

| Sample | Positive | Negative |
|---|---|---|
| 21A | * | |
| H$_2$O | * | |
| 8A | * | |
| 17A | * | |
| 20A | * | |
| 16N | | * |
| H$_2$O | * | |
| 17A | * | |
| 20A | * | |
| H$_2$O | * | |
| 8A | * | |
| 17A | | * |
| 20A | * | |
| 15A | | * |
| H$_2$O | | * |
| 8A | * | |
| 15A | * | |
| 17A | * | |
| 20A | * | |
| 16N | | * |
| H$_2$O | * | |
| 8A | * | |
| 15A | * | |
| 16N | | * |
| H$_2$O | * | |
| 8A | | * |
| 17A | * | |
| 20A | * | |
| 16N | | * |
| H$_2$O | * | |
| 8A | * | |
| 15A | * | |
| 17A | * | |
| 20A | * | |
| 16N | | * |
| 18N | | * |
| H$_2$O | | * |

Sequence Analysis

The first differential display sequence isolated from patients (FIG. 6) led us to suspect the presence of bacteria.

Summary of a FASTA analysis of this sequence is shown below and this indicates a very high similarity to sequences of prokaryotic origin.

| Sequences producing significant alignments: | (bits) | Value |
|---|---|---|
| gb\|AE000244.1\|AE000244 *Escherichia coli* K-12 MG1655 section . . . | 657 | 0.0 |
| dbj\|D90788.1\|D90788 *E. coli* genomic DNA, Kohara clone #277 (3 . . . | 657 | 0.0 |
| dbj\|D90787.1\|D90787 *E. coli* genomic DNA, Kohara clone #276 (3 . . . | 657 | 0.0 |
| emb\|X94992.1\|ECNARG *E. coli* nitrite extrusion gene and secon . . . | 657 | 0.0 |
| dbj\|D26057.1\|STYNARK *Salmonella typhimurium* genes for SmvA . . . | 156 | 2e-35 |
| gb\|AE000220.1\|AE000220 *Escherichia coli* K-12 MG1655 section . . . | 79 | 2e-12 |
| dbj\|D90757.1\|D90757 *Escherichia coli* genomic DNA. (27.3 - 2 . . . | 79 | 2e-12 |
| emb\|X69189.1\|ECNARXLO *E. coli* narXL operon and partial narK . . . | 79 | 2e-12 |
| emb\|X15996.1\|ECNARK *E. coli* narK gene and partial sequence o . . . | 79 | 2e-12 |
| gb\|AF026945.1\|AF026945 *Homo sapiens* cig64 mRNA, partial seq . . . | 57 | 1e-05 |
| gb\|U32804.1\|U32804 *Haemophilus influenzae* Rd section 119 of . . . | 43 | 0.18 |
| gb\|AC009276.9\|AC009276 *Homo sapiens* chromosome 7 clone RP11 . . . | 41 | 0.74 |
| gb\|AE003592.1\|AE003592 *Drosophila melanogaster* genomic scaf . . . | 41 | 0.74 |

| Sequences producing significant alignments: | (bits) | Value |
|---|---|---|
| gb\|AF098951.1\|AF098951 *Homo sapiens* breast cancer resistanc . . . | 41 | 0.74 |
| gb\|AF095856.1\|AF095856 *Homo sapiens* asthmatic clone 4 mRNA, . . . | 41 | 0.74 |
| gb\|AF095855.1\|AF095855 *Homo sapiens* asthmatic clone 3 mRNA, . . . | 41 | 0.74 |
| gb\|AF100329.1\|AF100329 *Dendrobium grex* Madame Thong-IN ovg1 . . . | 41 | 0.74 |
| gb\|AF013290.1\|AF013290 *Meloidogyne incognita* elongation fac . . . | 41 | 0.74 |
| emb\|X65318.2\|CVPGEMEX2 Cloning vector pGEMEX-2 | 41 | 0.74 |
| emb\|X65317.2\|CVPGEMEX1 Cloning vector pGEMEX-1 | 41 | 0.74 |
| gb\|L36849.1\|SYNSHBL Cloning vector pZEO (isolate SV1) phleo . . . | 39 | 3.0 |
| ref\|NM 015880.1\| *Homo sapiens* RIG-like 14-1 (LOC51047), mRNA | 39 | 3.0 |
| gb\|L36850.1\|SYNLACZ Cloning vector pZEO (isolate SVLacZ) be . . . | 39 | 3.0 |
| gb\|AE00349E.1\|AE003496 *Drosophila melanogaster* genomic scaf . . . | 39 | 3.0 |

Composite sequences from various patient samples generated using the primers described herein have been subjected to FASTA analysis. The results of these indicate the presence in OA tissue of *Janthinobacterium* or a bacterial species very closely related thereto. Two such analyses are presented below by way of example.

The forward and reverse composite sequence from affected tissue of patient 21 (FIG. 12) was found by Blastn search of the NCBI data-base to represent *Janthinobacterium*. This sequence was always found in OA patients.

The 3 best alignments of this sequence following a Blastn enquiry of Nov. 13, 2000 were:

```
gi|3201903|gb|AF067655.1|AF067655 Uncultured Duganella clon . . .    2730 0.0
gi|5738214|gb|AF174648.1|AF174648 Janthinobacterium lividum . . .    2714 0.0
gi|2832894|emb|Y08846.1|JL16SRRN J. lividum 16S rRNA gene            2714 0.0
```

The actual alignments were as follows:

```
>gi|3201903|gb|AF067655.1|AF067655 Uncultured Duganella clone CTHB-18 16S ribosomal
RNA gene, partial sequence
    Length = 1453
Score = 2730 bits (1377), Expect = 0.0
Identities = 1393/1400 (99%)
Strand = Plus/Plus Query:    44  catgcaagtcgaacggcagcacggagcttgctctggtggcgagtggcgaacgggtgagta  103
              |||| |||||||||||||||||||||||||||||||||||||||||||||||||||||||
Sbjct:    27  catgtaagtcgaacggcagcacggagcttgctctggtggcgagtggcgaacgggtgagta   86

Query:   104  atatatcggaacgtaccctagagtgggggataacgtagcgaaagttacgctaataccgca  163
              ||||||||||||||||||||||||||||||||||||||||||||||||||||||||||||
Sbjct:    87  atatatcggaacgtaccctagagtgggggataacgtagcgaaagttacgctaataccgca  146

Query:   164  tacgatctaaggatgaaagtgggggatcgcaagacctcatgctcgtggagcggccgatat  223
              ||||||||||||||||||||||||||||||||||||||||||||||||||||||||||||
Sbjct:   147  tacgatctaaggatgaaagtgggggatcgcaagacctcatgctcgtggagcggccgatat  206

Query:   224  ctgattagctagttggtagggtaaaagcctaccaaggcatcgatcagtagctggtctgag  283
              ||||||||||||||||||||||||||||||||||||||||||||||||||||||||||||
Sbjct:   207  ctgattagctagttggtagggtaaaagcctaccaaggcatcgatcagtagctggtctgag  266

Query:   284  aggacgaccagccacactggaactgagacacggtccagactcctacgggaggcagcagtg  343
              ||||||||||||||||||||||||||||||||||||||||||||||||||||||||||||
Sbjct:   267  aggacgaccagccacactggaactgagacacggtccagactcctacgggaggcagcagtg  326

Query:   344  gggaattttggacaatgggcgaaagcctgatccagcaatgccgcgtgagtgaagaaggcc  403
              ||||||||||||||||||||||||||||||||||||||||||||||||||||||||||||
Sbjct:   327  gggaattttggacaatgggcgaaagcctgatccagcaatgccgcgtgagtgaagaaggcc  386
```

```
Query:    404  ttcggghttgtaaagctctttttgtcagggaagaaacggtgagagctaatatctcttgctaa   463
               ||||||||||||||||||||||||||||||||||||||||||||||||||||||||||||
Sbjct:    387  ttcggghttgtaaagctctttttgtcagggaagaaacggtgagagctaatatctcttgctaa   446

Query:    464  tgacggtacctgaagaataagcaccggctaactacgtgccagcagccgcggtaatacgta   523
               ||||||||||||||||||||||||||||||||||||||||||||||||||||||||||||
Sbjct:    447  tgacggtacctgaagaataagcaccggctaactacgtgccagcagccgcggtaatacgta   506

Query:    524  gggtgcaagcgttaatcggaattactgggcgtaaagcgtgcgcaggcggttttgtaagtc   583
               ||||||||||||||||||||||||||||||||||||||||||||||||||||||||||||
Sbjct:    507  gggtgcaagcgttaatcggaattactgggcgtaaagcgtgcgcaggcggttttgtaagtc   566

Query:    584  tgatgtgaaatccccgggctcaacctgggaattgcattggagactgcaaggctagaatct   643
               ||||||||||||||||||||||||||||||||||||||||||||||||||||||||||||
Sbjct:    567  tgatgtgaaatccccgggctcaacctgggaattgcattggagactgcaaggctagaatct   626

Query:    644  ggcagaggggggtagaattccacgtgtagcagtgaaatgcgtagatatgtggaggaacac   703
               ||||||||||||||||||||||||||||||||||||||||||||||||||||||||||||
Sbjct:    627  ggcagaggggggtagaattccacgtgtagcagtgaaatgcgtagatatgtggaggaacac   686

Query:    704  cgatggcgaaggcagccccctgggtcaagattgacgctcatgcacgaaagcgtggggagc   763
               ||||||||||||||||||||||||||||||||||||||||||||||||||||||||||||
Sbjct:    687  cgatggcgaaggcagccccctgggtcaagattgacgctcatgcacgaaagcgtggggagc   746

Query:    764  aaacaggattagataccctggtagtccacgccctaaacgatgtctactagttgtcgggtc   823
               ||||||||||||||||||||||||||||||||||||||||||||||||||||||||||||
Sbjct:    747  aaacaggattagataccctggtagtccacgccctaaacgatgtctactagttgtcgggtc   806

Query:    824  ttaattgacttggtaacgcagctaacgcgtgaagtagaccgcctggggagtacggtcgca   883
               ||||||||||||||||||||||||||||||||||||||||||||||||||||||||||||
Sbjct:    807  ttaattgacttggtaacgcagctaacgcgtgaagtagaccgcctggggagtacggtcgca   866

Query:    884  agattaaaactcaaaggaattgacggggacccgcacaagcggtggatgatgtggattaat   943
               ||||||||||||||||||||||||||||||||||||||||||||||||||||||||||||
Sbjct:    867  agattaaaactcaaaggaattgacggggacccgcacaagcggtggatgatgtggattaat   926

Query:    944  tcgatgcaacgcgaaaaaccttacctacccttgacatggctggaatccttgagagatcag   1003
               ||||||||||||||||||||||||||||||||||||||||||||||||||||||||||||
Sbjct:    927  tcgatgcaacgcgaaaaaccttacctacccttgacatggctggaatccttgagagatcag   986

Query:   1004  ggagtgctcgaaagagaaccagtacacaggtgctgcatggctgtcgtcagctcgtgtcgt   1063
               ||||||||||||||||||||||||||||||||||||||||||||||||||||||||||||
Sbjct:    987  ggagtgctcgaaagagaaccagtacacaggtgctgcatggctgtcgtcagctcgtgtcgt   1046

Query:   1064  gagatgttgggttaagtcccgcaacgagcgcaacccttgtcattagttgctacgaaaggg   1123
               ||||||||||||||||||||||||||||||||||||||||||||||||||||||||||||
Sbjct:   1047  gagatgttgggttaagtcccgcaacgagcgcaacccttgtcattagttgctacgaaaggg   1106

Query:   1124  cactctaatgagactgccggtgacaaaccggaggaaggtggggatgacgtcaagtcctca   1183
               ||||||||||||||||||||||||||||||||||||||||||||||||||||||||||||
Sbjct:   1107  cactctaatgagactgccggtgacaaaccggaggaaggtggggatgacgtcaagtcctca   1166

Query:   1184  tggcccttatgggtagggcttcacacgtcatacaatggtacatacagagcgccgccaacc   1243
               ||||||||||||||||||||||||||||||||||||||||||||||||||||||||||||
Sbjct:   1167  tggcccttatgggtagggcttcacacgtcatacaatggtacatacagagcgccgccaacc   1226

Query:   1244  cgcgagggggagctaatcgcagaaagtgtatcgtagtccggattgtagtctgcaactcga   1303
               ||||||||||||||||||||||||||||||||||||||||||||||||||||||||||||
Sbjct:   1227  cgcgagggggagctaatcgcagaaagtgtatcgtagtccggattgtagtctgcaactcga   1286

Query:   1304  ctgcatgaagttggaatcgctagtaatcgcggatcagcatgtcncggtnaanacgttccc   1363
               |||||||||||||||||||||||||||||||||||||||||||| ||||  || ||||||
Sbjct:   1287  ctgcatgaagttggaatcgctagtaatcgcggatcagcatgtcgcggtgaatacgttccc   1346

Query:   1364  gggtcttgtacacaccgcccgtcacaccatgggagcgggttttaccagaagtaggtagct   1423
               ||||||||||||||||||||||||||||||||||||||||||||||||||||||||||||
Sbjct:   1347  gggtcttgtacacaccgcccgtcacaccatgggagcgggttttaccagaagtaggtagct   1406

Query:   1424  tanccncaaggagggcgctt   1443
               || || ||||||||||||||
Sbjct:   1407  taaccgtaaggagggcgctt   1426
```

-continued

```
>gi|5738214|gb|AF174648.1|AF174648 Janthinobacterium lividum 16S ribosomal RNA gene,
partial sequence
    Length = 1486
Score = 2714 bits (1369), Expect = 0.0
Identities = 1391/1400 (99%)
Strand = Plus/Plus Query:   44  catgcaagtcgaacggcagcacggagcttgctctggtggcgagtggcgaacgggtgagta  103
             ||||||||||||||||||||||||||||||||||||||||||||||||||||||||||||
Sbjct:   27  catgcaagtcgaacggcagcacggagcttgctctggtggcgagtggcgaacgggtgagta  86

Query:  104  atatatcggaacgtaccctagagtgggggataacgtagcgaaagttacgctaataccgca  163
             ||||||||||||||||||||||||||||||||||||||||||||||||||||||||||||
Sbjct:   87  atatatcggaacgtaccctagagtgggggataacgtagcgaaagttacgctaataccgca  146

Query:  164  tacgatctaaggatgaaagtgggggatcgcaagacctcatgctcgtggagcggccgatat  223
             ||||||||||||||||||||||||||||||||||||||||||||||||||||||||||||
Sbjct:  147  tacgatctaaggatgaaagtgggggatcgcaagacctcatgctcgtggagcggccgatat  206

Query:  224  ctgattagctagttggtagggtaaaagcctaccaaggcatcgatcagtagctggtctgag  283
             ||||||||||||||||||||||||||||||||||||||||||||||||||||||||||||
Sbjct:  207  ctgattagctagttggtagggtaaaagcctaccaaggcatcgatcagtagctggtctgag  266

Query:  284  aggacgaccagccacactggaactgagacacggtccagactcctacgggaggcagcagtg  343
             ||||||||||||||||||||||||||||||||||||||||||||||||||||||||||||
Sbjct:  267  aggacgaccagccacactggaactgagacacggtccagactcctacgggaggcagcagtg  326

Query:  344  gggaattttggacaatgggcgaaagcctgatccagcaatgccgcgtgagtgaagaaggcc  403
             ||||||||||||||||||||||||||||||||||||||||||||||||||||||||||||
Sbjct:  327  gggaattttggacaatgggcgaaagcctgatccagcaatgccgcgtgagtgaagaaggcc  386

Query:  404  ttcgggttgtaaagctcttttgtcagggaagaaacggtgagagctaatatctcttgctaa  463
             ||||||||||||||||||||||||||||||||||||||||||||||||||||||||||||
Sbjct:  387  ttcgggttgtaaagctcttttgtcagggaagaaacggtgagagctaatatctcttgctaa  446

Query:  464  tgacggtacctgaagaataagcaccggctaactacgtgccagcagccgcggtaatacgta  523
             ||||||||||||||||||||||||||||||||||||||||||||||||||||||||||||
Sbjct:  447  tgacggtacctgaagaataagcaccggctaactacgtgccagcagccgcggtaatacgta  506

Query:  524  gggtgcaagcgttaatcggaattactgggcgtaaagcgtgcgcaggcggttttgtaagtc  583
             ||||||||||||||||||||||||||||||||||||||||||||||||||||||||||||
Sbjct:  507  gggtgcaagcgttaatcggaattactgggcgtaaagcgtgcgcaggcggttttgtaagtc  566

Query:  584  tgatgtgaaatccccgggctcaacctgggaattgcattggagactgcaaggctagaatct  643
             ||||||||||||||||||||||||||||||||||||||||||||||||||||||||||||
Sbjct:  567  tgatgtgaaatccccgggctcaacctgggaattgcattggagactgcaaggctagaatct  626

Query:  644  ggcagaggggggtagaattccacgtgtagcagtgaaatgcgtagatatgtggaggaacac  703
             ||||||||||||||||||||||||||||||||||||||||||||||||||||||||||||
Sbjct:  627  ggcagaggggggtagaattccacgtgtagcagtgaaatgcgtagatatgtggaggaacac  686

Query:  704  cgatggcgaaggcagccccctgggtcaagattgacgctcatgcacgaaagcgtggggagc  763
             ||||||||||||||||||||||||||||||||||||||||||||||||||||||||||||
Sbjct:  687  cgatggcgaaggcagccccctgggtcaagattgacgctcatgcacgaaagcgtggggagc  746

Query:  764  aaacaggattagataccctggtagtccacgccctaaacgatgtctactagttgtcgggtc  823
             ||||||||||||||||||||||||||||||||||||||||||||||||||||||||||||
Sbjct:  747  aaacaggattagataccctggtagtccacgccctaaacgatgtctactagttgtcgggtc  806

Query:  824  ttaattgacttggtaacgcagctaacgcgtgaagtagaccgcctggggagtacggtcgca  883
             ||||||||||||||||||||||||||||||||||||||||||||||||||||||||||||
Sbjct:  807  ttaattgacttggtaacgcagctaacgcgtgaagtagaccgcctggggagtacggtcgca  866

Query:  884  agattaaaactcaaaggaattgacggggacccgcacaagcggtggatgatgtggattaat  943
             ||||||||||||||||||||||||||||||||||||||||||||||||||||||||||||
Sbjct:  867  agattaaaactcaaaggaattgacggggacccgcacaagcggtggatgatgtggattaat  926

Query:  944  tcgatgcaacgcgaaaaaccttacctacccttgacatggctggaatccttgagagatcag  1003
             |||||||||||||||||||||||||||||||||||||||||||||||||||| ||||| 
Sbjct:  927  tcgatgcaacgcgaaaaaccttacctacccttgacatggctggaatcctcgagagattga  986

Query: 1004  ggagtgctcgaaagagaaccagtacacaggtgctgcatggctgtcgtcagctcgtgtcgt  1063
             ||||||||||||||||||||||||||||||||||||||||||||||||||||||||||||
Sbjct:  987  ggagtgctcgaaagagaaccagtacacaggtgctgcatggctgtcgtcagctcgtgtcgt  1046
```

```
                                        -continued
Query:  1064  gagatgttgggttaagtcccgcaacgagcgcaacccttgtcattagttgctacgaaaggg  1123
              ||||||||||||||||||||||||||||||||||||||||||||||||||||||||||||
Sbjct:  1047  gagatgttgggttaagtcccgcaacgagcgcaacccttgtcattagttgctacgaaaggg  1106

Query:  1124  cactctaatgagactgccggtgacaaaccggaggaaggtggggatgacgtcaagtcctca  1183
              ||||||||||||||||||||||||||||||||||||||||||||||||||||||||||||
Sbjct:  1107  cactctaatgagactgccggtgacaaaccggaggaaggtggggatgacgtcaagtcctca  1166

Query:  1184  tggcccttatgggtagggcttcacacgtcatacaatggtacatacagagcgccgccaacc  1243
              ||||||||||||||||||||||||||||||||||||||||||||||||||||||||||||
Sbjct:  1167  tggcccttatgggtagggcttcacacgtcatacaatggtacatacagagcgccgccaacc  1226

Query:  1244  cgcgaggggagctaatcgcagaaagtgtatcgtagtccggattgtagtctgcaactcga  1303
              ||||||||||||||||||||||||||||||||||||||||||||||||||||||||||||
Sbjct:  1227  cgcgaggggagctaatcgcagaaagtgtatcgtagtccggattgtagtctgcaactcga  1286

Query:  1304  ctgcatgaagttggaatcgctagtaatcgcggatcagcatgtcncggtnaanacgttccc  1363
              |||||||||||||||||||||||||||||||||||||||||||| |||  || |||||||
Sbjct:  1287  ctgcatgaagttggaatcgctagtaatcgcggatcagcatgtcgcggtgaatacgttccc  1346

Query:  1364  gggtcttgtacacaccgcccgtcacaccatgggagcgggttttaccagaagtaggtagct  1423
              ||||||||||||||||||||||||||||||||||||||||||||||||||||||||||||
Sbjct:  1347  gggtcttgtacacaccgcccgtcacaccatgggagcgggttttaccagaagtaggtagct  1406

Query:  1424  tanccncaaggagggcgctt  1443
              || || ||||||||||||||
Sbjct:  1407  taaccgcaaggagggcgctt  1426

>gi|2832894|emb|Y08846.1|JL16SRRN J. lividum 16S rRNA gene
    Length = 1469
Score = 2714 bits (1369), Expect = 0.0
Identities = 1391/1400 (99%)
Strand = Plus/Plus Query:    44  catgcaagtcgaacggcagcacggagcttgctctggtggcgagtggcgaacgggtgagta  103
              ||||||||||||||||||||||||||||||||||||||||||||||||||||||||||||
Sbjct:    26  catgcaagtcgaacggcagcacggagcttgctctggtggcgagtggcgaacgggtgagta   85

Query:   104  atatatcggaacgtaccctagagtgggggataacgtagcgaaagttacgctaataccgca  163
              ||||||||||||||||||||||||||||||||||||||||||||||||||||||||||||
Sbjct:    86  atatatcggaacgtaccctagagtgggggataacgtagcgaaagttacgctaataccgca  145

Query:   164  tacgatctaaggatgaaagtgggggatcgcaagacctcatgctcgtggagcggccgatat  223
              ||||||||||||||||||||||||||||||||||||||||||||||||||||||||||||
Sbjct:   146  tacgatctaaggatgaaagtgggggatcgcaagacctcatgctcgtggagcggccgatat  205

Query:   224  ctgattagctagttggtagggtaaaagcctaccaaggcatcgatcagtagctggtctgag  283
              ||||||||||||||||||||||||||||||||||||||||||||||||||||||||||||
Sbjct:   206  ctgattagctagttggtagggtaaaagcctaccaaggcatcgatcagtagctggtctgag  265

Query:   284  aggacgaccagccacactggaactgagacacggtccagactcctacgggaggcagcagtg  343
              ||||||||||||||||||||||||||||||||||||||||||||||||||||||||||||
Sbjct:   266  aggacgaccagccacactggaactgagacacggtccagactcctacgggaggcagcagtg  325

Query:   344  gggaattttggacaatgggcgaaagcctgatccagcaatgccgcgtgagtgaagaaggcc  403
              ||||||||||||||||||||||||||||||||||||||||||||||||||||||||||||
Sbjct:   326  gggaattttggacaatgggcgaaagcctgatccagcaatgccgcgtgagtgaagaaggcc  385

Query:   404  ttcgggttgtaaagctcttttgtcagggaagaaacggtgagagctaatatctcttgctaa  463
              ||||||||||||||||||||||||||||||||||||||||||||||||||||||||||||
Sbjct:   386  ttcgggttgtaaagctcttttgtcagggaagaaacggtgagagctaatatctcttgctaa  445

Query:   464  tgacggtacctgaagaataagcaccggctaactacgtgccagcagccgcggtaatacgta  523
              ||||||||||||||||||||||||||||||||||||||||||||||||||||||||||||
Sbjct:   446  tgacggtacctgaagaataagcaccggctaactacgtgccagcagccgcggtaatacgta  505

Query:   524  gggtgcaagcgttaatcggaattactgggcgtaaagcgtgcgcaggcggttttgtaagtc  583
              ||||||||||||||||||||||||||||||||||||||||||||||||||||||||||||
Sbjct:   506  gggtgcaagcgttaatcggaattactgggcgtaaagcgtgcgcaggcggttttgtaagtc  565

Query:   584  tgatgtgaaatccccgggctcaacctgggaattgcattggagactgcaaggctagaatct  643
              ||||||||||||||||||||||||||||||||||||||||||||||||||||||||||||
Sbjct:   566  tgatgtgaaatccccgggctcaacctgggaattgcattggagactgcaaggctagaatct  625
```

-continued

```
Query:   644   ggcagaggggggtagaattccacgtgtagcagtgaaatgcgtagatatgtggaggaacac   703
               ||||||||||||||||||||||||||||||||||||||||||||||||||||||||||||
Sbjct:   626   ggcagaggggggtagaattccacgtgtagcagtgaaatgcgtagatatgtggaggaacac   685

Query:   704   cgatggcgaaggcagcccctgggtcaagattgacgctcatgcacgaaagcgtggggagc    763
               ||||||||||||||||||||||||||||||||||||||||||||||||||||||||||||
Sbjct:   686   cgatggcgaaggcagcccctgggtcaagattgacgctcatgcacgaaagcgtggggagc    745

Query:   764   aaacaggattagataccctggtagtccacgccctaaacgatgtctactagttgtcgggtc   823
               ||||||||||||||||||||||||||||||||||||||||||||||||||||||||||||
Sbjct:   746   aaacaggattagataccctggtagtccacgccctaaacgatgtctactagttgtcgggtc   805

Query:   824   ttaattgacttggtaacgcagctaacgcgtgaagtagaccgcctggggagtacggtcgca   883
               ||||||||||||||||||||||||||||||||||||||||||||||||||||||||||||
Sbjct:   806   ttaattgacttggtaacgcagctaacgcgtgaagtagaccgcctggggagtacggtcgca   865

Query:   884   agattaaaactcaaaggaattgacggggacccgcacaagcggtggatgatgtggattaat   943
               ||||||||||||||||||||||||||||||||||||||||||||||||||||||||||||
Sbjct:   866   agattaaaactcaaaggaattgacggggacccgcacaagcggtggatgatgtggattaat   925

Query:   944   tcgatgcaacgcgaaaaaccttacctacccttgacatggctggaatccttgagagatcag   1003
               |||||||||||||||||||||||||||||||||||||||||||||||||   |||||||  |
Sbjct:   926   tcgatgcaacgcgaaaaaccttacctacccttgacatggctggaatccccgagagattgg   985

Query:   1004  ggagtgctcgaaagagaaccagtacacaggtgctgcatggctgtcgtcagctcgtgtcgt   1063
               ||||||||||||||||||||||||||||||||||||||||||||||||||||||||||||
Sbjct:   986   ggagtgctcgaaagagaaccagtacacaggtgctgcatggctgtcgtcagctcgtgtcgt   1045

Query:   1064  gagatgttgggttaagtcccgcaacgagcgcaaccccttgtcattagttgctacgaaaggg   1123
               ||||||||||||||||||||||||||||||||||||||||||||||||||||||||||||
Sbjct:   1046  gagatgttgggttaagtcccgcaacgagcgcaaccccttgtcattagttgctacgaaaggg   1105

Query:   1124  cactctaatgagactgccggtgacaaaccggaggaaggtggggatgacgtcaagtcctca   1183
               ||||||||||||||||||||||||||||||||||||||||||||||||||||||||||||
Sbjct:   1106  cactctaatgagactgccggtgacaaaccggaggaaggtggggatgacgtcaagtcctca   1165

Query:   1184  tggcccttatgggtagggcttcacacgtcatacaatggtacatacagagcgccgccaacc   1243
               ||||||||||||||||||||||||||||||||||||||||||||||||||||||||||||
Sbjct:   1166  tggcccttatgggtagggcttcacacgtcatacaatggtacatacagagcgccgccaacc   1225

Query:   1244  cgcgaggggagctaatcgcagaaagtgtatcgtagtccggattgtagtctgcaactcga    1303
               ||||||||||||||||||||||||||||||||||||||||||||||||||||||||||||
Sbjct:   1226  cgcgaggggagctaatcgcagaaagtgtatcgtagtccggattgtagtctgcaactcga    1285

Query:   1304  ctgcatgaagttggaatcgctagtaatcgcggatcagcatgtcncggtnaanacgttccc   1363
               ||||||||||||||||||||||||||||||||||||||||||||||| ||||  || ||||||||
Sbjct:   1286  ctgcatgaagttggaatcgctagtaatcgcggatcagcatgtcgcggtnaatacgttccc   1345

Query:   1364  gggtcttgtacacaccgcccgtcacaccatgggagcgggttttaccagaagtaggtagct   1423
               ||||||||||||||||||||||||||||||||||||||||||||||||||||||||||||
Sbjct:   1346  gggtcttgtacacaccgcccgtcacaccatgggagcgggttttaccagaagtaggtagct   1405

Query:   1424  tanccncaaggagggcgctt   1443
               || || ||||||||||||||
Sbjct:   1406  taaccgcaaggagggcgctt   1425
```

A composite sequence (705 nucleotides) from affected tissue in patient 17 using forward primer F7 was similarly analysed and the four best alignments from a database containing 671,573 sequences were:

```
gb|AF174648.1|AF174648  Janthinobacterium lividum 16S riboso . . .   1315  0.0 gb|AF067655.1|AF067655  Uncultured Duganella clone CTHB-18 1 . . .   1315  0.0 dbj|AB021388.1|AB021388  Pseudomonas mephitica DNA for 16S r . . .   1315  0.0 emb|Y08846.1|JL16SRRN  J. lividum 16S rRNA gene                      1315  0.0
```

The actual alignment for the first sequence on the list is shown below:

```
gb|AF174648.1|AF174648 Janthinobacterium lividum 16S ribosomal RNA gene,
partial sequence
    Length = 1486
Score = 1315 bits (658), Expect = 0.0
Identities = 681/689 (98%), Gaps = 3/689 (0%)
Strand = Plus/Plus Query:   19  gagcttgctctggtggcgagtggcgaacgggtgagtaatatatcggaacgtaccctagag   78
             ||||||||||||||||||||||||||||||||||||||||||||||||||||||||||||
Sbjct:   50  gagcttgctctggtggcgagtggcgaacgggtgagtaatatatcggaacgtaccctagag   109

Query:   79  tgggggataacgtagcgaaagttacgctaataccgcatacgatctaaggatgaaagtggg   138
             ||||||||||||||||||||||||||||||||||||||||||||||||||||||||||||
Sbjct:  110  tgggggataacgtagcgaaagttacgctaataccgcatacgatctaaggatgaaagtggg   169

Query:  139  ggatcgcaagacctcatgctcgtggagcggccgatatctgattagctagttggtagggta   198
             ||||||||||||||||||||||||||||||||||||||||||||||||||||||||||||
Sbjct:  170  ggatcgcaagacctcatgctcgtggagcggccgatatctgattagctagttggtagggta   229

Query:  199  aaagcctaccaaggcatcgatcagtagctggtctgagaggacgaccagccacactggaac   258
             ||||||||||||||||||||||||||||||||||||||||||||||||||||||||||||
Sbjct:  230  aaagcctaccaaggcatcgatcagtagctggtctgagaggacgaccagccacactggaac   289

Query:  259  tgagacacggtccagactcctacgggaggcagcagtggggaattttggacaatgggcgaa   318
             ||||||||||||||||||||||||||||||||||||||||||||||||||||||||||||
Sbjct:  290  tgagacacggtccagactcctacgggaggcagcagtggggaattttggacaatgggcgaa   349

Query:  319  a--ctgaatccagcaatgccgcgtgagtgaagaaggccttcggggttgtaaagctcttttg   376
             |  ||||  |||||||||||||||||||||||||||||||||||||||||||||||||||
Sbjct:  350  agcctga-tccagcaatgccgcgtgagtgaagaaggccttcggggttgtaaagctcttttg   408

Query:  377  tcagggaagaaacggtgagagctaatatctcttgctaatgacggtacctgaagaataagc   436
             ||||||||||||||||||||||||||||||||||||||||||||||||||||||||||||
Sbjct:  409  tcagggaagaaacggtgagagctaatatctcttgctaatgacggtacctgaagaataagc   468

Query:  437  accggctaactacgtgccagcagccgcggtaatacgtagggtgcaagcgttaatcggaat   496
             ||||||||||||||||||||||||||||||||||||||||||||||||||||||||||||
Sbjct:  469  accggctaactacgtgccagcagccgcggtaatacgtagggtgcaagcgttaatcggaat   528

Query:  497  tactgggcgtaaagcgtgcgcaggcggttttgtaagtctgatgtgaaatccccgggctca   556
             ||||||||||||||||||||||||||||||||||||||||||||||||||||||||||||
Sbjct:  529  tactgggcgtaaagcgtgcgcaggcggttttgtaagtctgatgtgaaatccccgggctca   588

Query:  557  acctgggaattgcattggagactgcaaggctagaatctggcagaggggggtagaattcca   616
             ||||||||||||||||||||||||||||||||||||||||||||||||||||||||||||
Sbjct:  589  acctgggaattgcattggagactgcaaggctagaatctggcagaggggggtagaattcca   648

Query:  617  cgtgtagcagtraaatgcgtagatatgtggaggaacaccgatggcgaagsvagcccctg   676
             |||||||||||| |||||||||||||||||||||||||||||||||||   |||||||||
Sbjct:  649  cgtgtagcagtgaaatgcgtagatatgtggaggaacaccgatggcgaaggcagcccctg   708

Query:  677  ggtcaagawtgacgctcatgcacaaaagc   705
             ||||||||  |||||||||||||  ||||
Sbjct:  709  ggtcaagattgacgctcatgcacgaaagc   737
```

Isolation of RNA and DNA from Synovial Fluid (SF)

The samples discussed previously were from biopsies but in a significant advance, it has now also been shown that a diagnosis can be made from a sample of synovial fluid which can be obtained without surgery in a much less invasive and traumatic procedure. A suitable protocol is described below.

After collection of SF from the patient the SF was stored at 4° C. and after no more than 20 minutes it was centrifuged at 13000 rpm (approx. 12500 g) for 30 minutes at 4° C. The supernatant was removed and the pellet was stored at −72° C. until RNA/DNA isolation. 1 ml of TRIzol solution was added to the pellet. The pellet was dissolved by vortexing and then incubated at room temperature for 10 minutes. 0.2 ml of chloroform was added to the solution and it was then mixed by vortexing and then incubated at room temperature for 15 minutes.

The solution was then centrifuged at 13000 rpm for 15 minutes at 4° C. The upper, aqueous phase was removed and RNA was isolated as described before. 0.3 ml of ethanol was added to the phenol-chloroform phase and the solution was then mixed by vortexing. The solution was then incubated at room temperature for 15 minutes. It was then centrifuged at 2000 rpm (approx. 4500) for 5 minutes at 4° C.

The supernatant was removed and the pellet was washed three times in 0.5 ml 0.1 M NaCitrate with 10% ethanol. After each wash it was centrifuged at 2000 rpm (approx. 4500 g) for 5 minutes at 4° C. and the supernatant was discarded. After the last wash the pellet was air-dried for 30 minutes at room temperature. The pellet was resuspended in 80 µl of 8 mM NaOH.

Example 2

Antibiotic Treatment of Patients with Osteoarthritis—Clinical Aspects

In this study an antibiotic effective against a wide range of Gram-negative and Gram-positive bacteria was used.

Introduction:

Thirty patients were diagnosed and treated for one month with the antibiotic known generically internationally as Doxycycline, this was purchased as Vibramycin from Pfizer. Samples from synovial fluid were taken before and after treatment.

Methods:

We identified 30 patients that had clinical and radiological signs of Osteoarthritis. These patients were informed and signed a paper according to the instructions from the ethical committee (Northern Norway Health Region 5).

We used the KOOS (Knee Injury and Osteoarthritis Outcome Score) [Roos et al: Development of a self-administered outcome measure. Journal of Orthopaedic and Sports Physical Therapy 78(2): 88-96, 1998] and the Lysholm score [Ref. Tegner and Lysholm: Rating systems in the Evaluation of Knee Ligament Injuries. Clinical Orthopaedics an Related Research Number 198 September 1985: 43-49.]

During the first visit we took a sample from the synovial fluid. Standard technique, upper lateral portal, using a 10 ml. syringe. If there was too little fluid and we did not aspirate synovial fluid at once, we injected 5-10 ml. physiological saline water and again aspirated. The samples were immediately put into an icebox and brought to the lab. All the patients were given Vibramycin 100 mg daily for 4 weeks. From the patients where we found the bacteria, we took new synovial-fluid samples using the same technique.

Clinical Results:

We observed improvement.

It is important to note that in this scoring system higher values means that the patients are better. Low values more symptoms, pain e.g.

All values improved in this study. A particularly significant improvement is considered when p values are ≦0.05.

KOOS: These parameters were analysed.

Symptoms
Activity of daily living
Sport
Quality of daily living
Pain
Lysholm:
    0-100. With 100 is the best score possible and 0 is the worst.

The results of these tests are presented in graphical form in FIGS. 16 to 21.

Table 3 below show a summary of the response to antibiotic treatment with tetracycline for four weeks as determined by direct questions to the patients on how they felt.

| Sample/Patient | Status after 4 weeks of treatment |
|---|---|
| 2 | improved |
| 3 | unchanged |
| 4 | unchanged |
| 5 | unchanged |
| 6 | improved |
| 7 | improved |
| 8 | unchanged |
| 9 | improved |
| 10 | improved |
| 11 | unchanged |
| 12 | unchanged |
| 13 | improved |
| 14 | improved |
| 15 | unchanged |
| 16 | improved |
| 17 | unchanged |
| 18 | unchanged |
| 19 | unchanged |
| 20 | unchanged |
| 21 | unchanged |
| 22 | unchanged |
| 23 | unchanged |
| 24 | unchanged |
| 25 | unchanged |
| 26 | improved |
| 34 | improved |

Conclusion

These results support our hypothesis that osteoarthritis can be treated with antibiotics. Vibramycin improved all the clinical scores for the patient.

---

The invention claimed is:

1. A method of treating a bacterial infection which is responsible for osteoarthritis in a subject, comprising administering to the subject, in an amount effective to treat a bacterial infection responsible for osteoarthritis, doxycycline and a second antibacterial agent or DNAse I, wherein the second antibacterial agent is clariththromycin, levofloxacin, mercaptoethylguanidine, ciprofloxacinlactate, tobramycin, ceftazidimpentathydrate, gentamicin, ciproxin, rifampicin, trimetroprim or sulfamethoxazole.

2. A method of reducing the development of advanced stage osteoarthritis in a subject, comprising administering to the subject, in an amount effective to treat a bacterial infection responsible for osteoarthritis, doxycycline and a second antibacterial agent or DNAse I, wherein the second antibacterial agent is clariththromycin, levofloxacin, mercaptoethylguanidine, ciprofloxacinlactate, tobramycin, ceftazidimpentathydrate, gentamicin, ciproxin, rifampicin, trimetroprim or sulfamethoxazole.

3. The method of claim 1 wherein said doxycycline or second antibacterial agent is effective against *Janthinobacterium*.

4. The method of claim 1 wherein the method comprises administering two antibacterial agents.

5. The method of claim 1 wherein the second antibacterial agent or DNAse I is in a form suitable for injection.

6. The method of claim 2 wherein said second antibacterial agent is effective against *Janthinobacterium*.

7. The method of claim 2 wherein the method comprises administering two antibacterial agents.

8. The method of claim 2 wherein the second antibacterial agent or DNAse I is in a form suitable for injection.

9. The method of claim 1, wherein the doxycycline is administered orally.

10. The method of claim 2, wherein the doxycycline is administered orally.

* * * * *

UNITED STATES PATENT AND TRADEMARK OFFICE
CERTIFICATE OF CORRECTION

PATENT NO. : 8,349,816 B2  
APPLICATION NO. : 11/703887  
DATED : January 8, 2013  
INVENTOR(S) : Mohamed Raafat El-Gewely It is certified that error appears in the above-identified patent and that said Letters Patent is hereby corrected as shown below:

Please amend the title page of issued U.S. Patent No. 8,349,816 to read:

item (62) Division of application No. 10/480,775, filed as application No. PCT/GB02/02771 on June 17, 2002.

Signed and Sealed this
Fourteenth Day of October, 2014

Michelle K. Lee
*Deputy Director of the United States Patent and Trademark Office*